(12) United States Patent
Hanaoka et al.

(10) Patent No.: US 10,815,379 B2
(45) Date of Patent: Oct. 27, 2020

(54) PH SENSITIVE FLUORESCENT PROBE

(71) Applicant: The University of Tokyo, Tokyo (JP)

(72) Inventors: Kenjiro Hanaoka, Tokyo (JP); Yu Kagami, Tokyo (JP); Tetsuo Nagano, Tokyo (JP); Yasuteru Urano, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 400 days.

(21) Appl. No.: 15/561,444

(22) PCT Filed: Jan. 15, 2016

(86) PCT No.: PCT/JP2016/051119
§ 371 (c)(1),
(2) Date: Dec. 8, 2017

(87) PCT Pub. No.: WO2016/157937
PCT Pub. Date: Oct. 6, 2016

(65) Prior Publication Data
US 2018/0118943 A1 May 3, 2018

Related U.S. Application Data

(60) Provisional application No. 62/261,438, filed on Dec. 1, 2015.

(30) Foreign Application Priority Data

Mar. 27, 2015 (JP) .................. 2015-065543

(51) Int. Cl.
| | | |
|---|---|---|
| C09B 11/26 | (2006.01) | |
| G01N 33/52 | (2006.01) | |
| C12Q 1/04 | (2006.01) | |
| C07F 7/12 | (2006.01) | |
| C09K 11/06 | (2006.01) | |
| G01N 21/80 | (2006.01) | |
| G01N 33/48 | (2006.01) | |
| C07F 7/10 | (2006.01) | |
| C07F 7/08 | (2006.01) | |
| C09B 11/28 | (2006.01) | |
| G01N 21/77 | (2006.01) | |

(52) U.S. Cl.
CPC ............ *C09B 11/26* (2013.01); *C07F 7/0812* (2013.01); *C07F 7/10* (2013.01); *C07F 7/12* (2013.01); *C09B 11/28* (2013.01); *C09K 11/06* (2013.01); *C12Q 1/04* (2013.01); *G01N 21/80* (2013.01); *G01N 33/48* (2013.01); *G01N 33/52* (2013.01); *C09K 2211/1018* (2013.01); *G01N 2021/7786* (2013.01)

(58) Field of Classification Search
CPC .. C07F 7/10; C07F 7/12; C07F 7/0182; C09B 11/26; C09B 11/28; C09K 11/06; C09K 211/1018; C12Q 1/04; G01N 21/80; G01N 33/48; G01N 33/52; G01N 2021/7786; G01N 21/78
See application file for complete search history.

(56) References Cited

U.S. PATENT DOCUMENTS 9,784,732 B2 * 10/2017 Urano .................. C07D 405/14
2014/0248654 A1    9/2014 Urano et al.
2015/0044776 A1    2/2015 Cong et al.

FOREIGN PATENT DOCUMENTS

| CN | 102659744 A1 | 9/2012 |
|---|---|---|
| WO | WO 2013/035767 A1 | 3/2013 |
| WO | WO 2013/134686 A1 | 9/2013 |

OTHER PUBLICATIONS

Myochin et al.(J. Am. Chem. Soc. (Mar. 12, 2015) 137: 4759-4765 (Year: 2015).*
Defintion of "general" downloaded from https://www.thefreedictionary.com/gneral on Dec. 8, 2019 (Year: 2019).*
Defintion of "derivative" downloaded from https://www.merriam-webster.com/dictionary/derivative on Dec. 8, 2019 (Year: 2019).*
Aigner, D., et al., New fluorescent pH sensors based on covalently linkable PET rhodamines, Talanta, vol. 99, pp. 194-201, 2012.
Asanuma, D., et al., Acidic-pH-Activatable Fluorescence Probes for Visualizing Exocytosis Dynamics, Angewandte Chemie, International Edition, vol. 53, No. 24, pp. 6085-6089, 2014.
Guan, X., et al., Development of a new rhodamine-based FRET platform and its application as a $Cu^{2+}$ probe, Organic & Biomolecular Chemistry, vol. 12, No. 23, pp. 3944-3949, 2014.

(Continued)

*Primary Examiner* — Susan M Hanley
(74) *Attorney, Agent, or Firm* — Knobbe, Martens, Olson & Bear, LLP

(57) ABSTRACT

Fluorescent probes and their salts have high fluorescence quantum yield and high resistance to photobleaching suitable for visualizing various pH environments within cells such as weakly basic, neutral, and weakly acidic environments. The fluorescent probes can have the following structure:

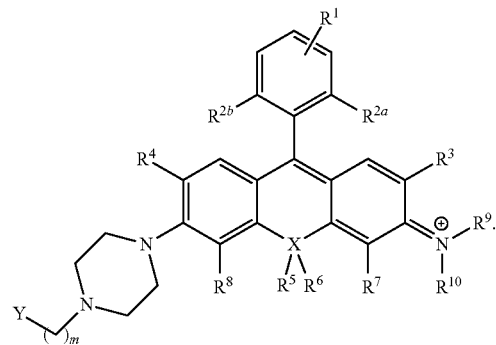

27 Claims, 11 Drawing Sheets

(56) References Cited

OTHER PUBLICATIONS

International Search Report, dated Apr. 5, 2016, in International Application No. PCT/JP2016/051119.

Isa, M., et al., High-Throughput Screening System to Identify Small Molecules That Induce Internalization and Degradation of HER2, ACS Chemical Biology, vol. 9, No. 10, pp. 2237-2241, 2014.

Zhang, Y-R., et al., A ratiometric fluorescent probe for sensing HOCl based on a coumarin-rhodamine dyad, Chemical Communications, vol. 50, No. 91, pp. 14241-14244, 2014.

Casey, J.R., et al., Sensors and regulators of intracellular pH, Nat. Rev. Mol. Cell Biol., vol. 11, pp. 50-61, 2010.

Han, J., et al., Fluorescent Indicators for Intracellular pH, Chem. Rev. vol. 110, pp. 2709-2728, 2010.

\* cited by examiner (a) SiRpH5

$$\text{Ratio} = \frac{Em_{690-750nm} (Ex. 580\ nm)}{Em_{690-750nm} (Ex. 670\ nm)}$$

PH SENSITIVE FLUORESCENT PROBE

PRIORITY AND CROSS REFERENCE TO RELATED APPLICATIONS

This application is the U.S. National Phase Application under 35 U.S.C. § 371 of International Application No. PCT/JP2016/051119, filed Jan. 15, 2016, designating the U.S. and published as WO 2016/157937 A1 on Oct. 6, 2016, which claims the benefit of Japanese Application No. JP 2015-065543, filed Mar. 27, 2015, and U.S. Provisional Application No. 62/261,438, filed Dec. 1, 2015. Any and all applications for which a foreign or a domestic priority is claimed is/are identified in the Application Data Sheet filed herewith and is/are hereby incorporated by reference in their entirety under 37 C.F.R. § 1.57.

TECHNICAL FIELD

The present invention relates to a novel pH-sensitive fluorescent probe and to a method for measuring acidic regions within cells using the same.

BACKGROUND ART

Cells carry out a variety of biochemical reactions, such as metabolism of proteins and organic compounds taken up, and synthesis and transport of cell structural components, at high spatiotemporal resolution and maintain life functions. Various organelles are present within cells to carry out these biochemical reactions efficiently, and each organelle maintains an optimum, unique pH for the various biochemical reactions (Non-patent Reference 1).

Since the pH is an important regulatory factor for cell function, changing the pH of an organelle greatly changes the function of the organelle. For example, in the endocytosis pathway that decomposes proteins taken up into the cell, the pH in the endosome acidifies as the endosome matures from 6.3 (early endosome) 5.5 (late endosome) 4.7 (lysosome), and the biochemical reactions that occur within the endosome also change accordingly from protein selection (early endosome) to protein decomposition (lysosome). Thus, since the pH within a cell is closely related to the chemical reactions that occur within the cell, measuring the intracellular pH is important for explaining the life phenomena that occur within a cell.

Fluorescence imaging has been the most widely used method for detecting intracellular pH in recent years. Fluorescence imaging uses a pH-sensitive fluorescent probe (abbreviated hereinafter as pH probe) based on an organic small-molecule fluorescent dye and a fluorescent protein. The pH probe has the characteristic of greatly changing fluorescence characteristics as the nearby pH changes. Detecting this change in fluorescence characteristics by an instrument such as a fluorescence microscope or plate reader makes it possible to measure the pH within a living cell conveniently.

pH probes include off/on type probes in which the fluorescence intensity rises greatly as the pH changes and ratio type probes in which the absorption wavelength or fluorescence wavelength changes greatly as the pH changes.

An off/on type pH probe has the advantage that it can be utilized even in relatively simple optical systems since excitation and fluorescence detection are carried out at only one wavelength each. However, it is difficult to measure the pH inside a cell quantitatively using an off/on type pH probe because increases and decreases in the probe concentration with cell contraction, leakage of the probe outside the cell, and the like are observed as increases and decreases in fluorescence intensity, that is, changes in pH.

A ratio type pH probe carries out excitation or fluorescence detection at two wavelengths, calculates the ratio of fluorescence intensity thereof, and observes the changes in the ratio value as changes in pH. Therefore, an optical system suitable for ratio measurement, such as an excitation light-switching device or multiple fluorescence detectors, is necessary to use a ratio type pH probe. On the other hand, an excellent characteristic of ratio type pH probes is that measurement errors due to factors other than changes in pH can be lessened since the ratio value does not change even if the probe concentration fluctuates. Therefore, the use of a ratio type pH probe makes it possible to measure the pH within a cell quantitatively. Ratio type pH probes consequently contribute greatly to explaining life phenomena associated with changes in pH.

There are two types of ratio type pH probe widely used today in biochemical research: the seminaphthorhodafluors (SNARF) and 2',7'-bis-(2-carboxyethyl)-5- (and -6-)carboxyfluoresceins (BCECF) shown in FIG. 1.

The most widely used pH probe "SNARF-1" (FIG. 1 (a)) is a one wavelength excitation/two wavelength photometric type; it enables ratio imaging when excited by light of 488 nm and fluorescence detection is carried out at 580 nm and 640 nm. SNARF-1 is used mainly for pH measurement of the cytoplasm because it is mainly localized in the cytoplasm and has a $pK_a$ (=7.5) suited to the pH fluctuation zone of the cytoplasm. Giant molecules such as proteins and microorganisms can also be labeled using an active ester form of SNARF, and the course of endocytosis of the target cell can be visualized. The disadvantages of SNARF-1 are said to be that the fluorescence quantum yield is relatively low (acidic side 0.03, basic side 0.09), the probe is sensitive to temperature and environment (the fluorescence decreases 25% with a change of 25° C. 37° C., and the fluorescence also decreases upon interaction with proteins), and is susceptible to photobleaching (Non-patent Reference 2). SNARF-4F, a SNARF derivative with the $pK_a$ lowered to 6.3, is also used to visualize acidification of the cytoplasm.

The next widely used "BCECF" (FIG. 1 (b)) is a two wavelength excitation/one wavelength fluorescence type; ratio imaging becomes possible when it is excited at 440 nm which is an isosbestic point and 488 nm near the peak top, and fluorescence detection is carried out at 535 nm. BCECF is used mainly in pH measurement of the cytoplasm because it is localized in the cytoplasm and has a $pK_a$ (=7.0) suited to the pH fluctuation zone of the cytoplasm. The disadvantages of BCECF are said to be that, while the absorbance and fluorescence quantum yield are high on the basic side, the absorbance and fluorescence quantum yield are low on the acidic side, ratio imaging is difficult due to large differences in luminance, and the probe is susceptible to photobleaching in the same way as fluorescein, which is the main skeleton. BCECF derivatives having different $pK_a$ are also not marketed.

Thus, conventional ratio type pH probes were developed based on a seminaphthorhodafluor or fluorescein skeleton which have a low fluorescence quantum yield, are temperature- and environment-dependent, and susceptible to photobleaching. The problem was therefore that long-term imaging was difficult and accurate pH measurement was difficult due to environmental factors such as the surrounding temperature and the environment of the organelle. pH probe derivatives having various $pK_a$ have also scarcely been developed by organochemical modification because structural modification of the probe molecule is difficult.

PRIOR ART REFERENCES

Non-Patent References

Non-Patent Reference 1: Nat. Rev. Mol. Cell Biol., 2010, 11, 50-61
Non-patent Reference 2: Chem. Rev. 2010, 110, 2709-2728

SUMMARY

The purpose of the present invention is to provide a pH probe having a high quantum fluorescence yield and high resistance to photobleaching that is suitable for visualization of various pH environments within a cell such as weakly basic, neutral, and weakly acidic environments.

When the present inventors conducted in-depth studies to solve the above problems, they discovered that, when they conducted various studies in the belief that the problems posed by existing pH probes cannot be solved by developing a ratio type pH probe using an Si-based rhodamine skeleton having high fluorescence quantum yield and high photobleaching resistance as had been developed by the present inventors in recent years, the pKa of the pH probe can be adjusted easily by introducing a piperazine ring into an asymmetric Si-based rhodamine skeleton and also introducing an electron-withdrawing group onto a piperazine ring amino group, and completed the present invention.

Specifically, the present invention provides:

[1] A compound represented by the following general formula (I):

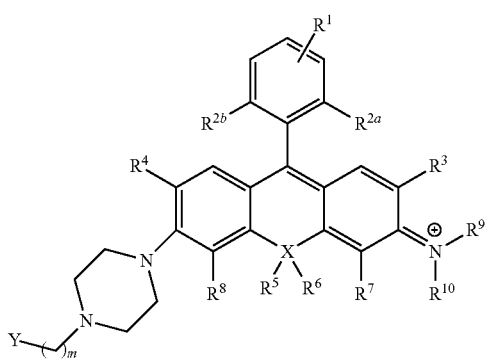

wherein,
$R^1$ is a hydrogen atom or from one to three of the same or different monovalent substituents present on the benzene ring;
$R^{2a}$ and $R^{2b}$ are, each independently, a hydrogen or a monovalent substituent, but $R^{2a}$ and $R^{2b}$ are not both hydrogen;
$R^3$ and $R^4$ are, each independently, a hydrogen atom, $C_{1-6}$ alkyl group, or halogen atom;
$R^5$ and $R^6$ are, when present, each independently, a $C_{1-6}$ alkyl group or aryl group,
here, when X is an oxygen atom, $R^5$ and $R^6$ are not present,
when X is a phosphorus atom, one of —$R^5$ and —$R^6$ may be =O;

$R^7$ and $R^8$ are, each independently, a hydrogen atom, $C_{1-6}$ alkyl group, or halogen atom;
$R^9$ and $R^{10}$ are, each independently, a hydrogen atom or $C_{1-6}$ alkyl group,
$R^9$ or $R^{10}$, together with $R^3$ or $R^7$, may form a five- to seven-membered heterocyclyl or heteroaryl including the nitrogen atoms to which $R^9$ or $R^{10}$ is bonded, may also contain from one to three hetero atoms selected from the group consisting of an oxygen atom, nitrogen atom, and sulfur atom as ring members, and the heterocyclyl or heteroaryl may also be substituted by a $C_{1-6}$ alkyl, $C_{2-6}$ alkenyl, or $C_{2-6}$ alkynyl, $C_{6-10}$ aralkyl group, or $C_{6-10}$ alkyl-substituted alkenyl group;
Y is a substituted or unsubstituted aryl group or heteroaryl group;
X is a silicon atom, oxygen atom, carbon atom, phosphorus atom, or germanium atom;
m is an integer of 0-6;
or a salt thereof.

[2] The compound according to [1] wherein Y is a substituted or unsubstituted phenyl group, or a salt thereof.

[3] The compound according to [2] wherein Y is a phenyl group, phenyl group substituted by a fluorine atom, or phenyl group substituted by a sulfonyl group, or a salt thereof.

[4] The compound according to any one of [1]-[3] wherein m is 0 or 1, or a salt thereof.

[5] The compound according to any one of [1]-[4] wherein at least one $R^1$ is selected from a carboxy group, alkyl group having a carboxy group, ester group, alkyl ester group, amino group, amide group, alkylamino group, isothiocyanate group, sulfonyl chloride group, haloalkyl group, haloacetamide group, azide group, or alkynyl group, or a salt thereof.

[6] The compound according to [5] wherein at least one $R^1$ is a carboxy group, alkyl group having a carboxyl group, amino group, or amide group, or a salt thereof.

[7] The compound according to any one of [1]-[6] wherein the monovalent substituent in $R^{2a}$ and $R^{2b}$ is a $C_{1-6}$ alkyl group, $C_{1-6}$ alkoxy group, or halogen atom, or a salt thereof.

[8] The compound according to [7] wherein one of $R^{2a}$ and $R^{2b}$ is hydrogen and the other is a $C_{1-6}$ alkyl group, $C_{1-6}$ alkoxy group, or halogen atom, or a salt thereof.

[9] The compound according to [7] wherein both of $R^{2a}$ and $R^{2b}$ are $C_{1-6}$ alkyl groups, or a salt thereof.

[10] The compound according to [1] represented by the following general formula (II):

wherein, $R^1$-$R^{2b}$, $R^4$-$R^8$, $R^{10}$, X, Y, and m are as defined in general formula (I), and $R^{11}$-$R^{24}$ are, each independently, a hydrogen atom, $C_{1-6}$ alkyl group, or halogen atom), or a salt thereof.

[11] The compound according to [10] wherein Y is a substituted or unsubstituted phenyl group, or a salt thereof.

[12] The compound according to [11] wherein Y is a phenyl group, phenyl group substituted by a fluorine atom, or phenyl group substituted by a sulfonyl group, or a salt thereof.

[13] The compound according to [11] or [12] wherein m is 0 or 1, or a salt thereof.

[14] The compound according to any one of [10]-[13] wherein at least one $R^1$ is selected from a carboxy group, alkyl group having a carboxy group, ester group, alkyl ester group, amino group, amide group, alkylamino group, isothiocyanate group, sulfonyl chloride group, haloalkyl group, haloacetamide group, azide group, or alkynyl group, or a salt thereof.

[15] The compound according to [14] wherein at least one $R^1$ is a carboxy group, alkyl group having a carboxyl group, amino group, or amide group, or a salt thereof.

[16] The compound according to any one of [10]-[15] wherein the monovalent substituent in $R^{2a}$ and $R^{2b}$ is a $C_{1-6}$ alkyl group, $C_{1-6}$ alkoxy group, or halogen atom, or a salt thereof.

[17] The compound according to [16] wherein one of $R^{2a}$ and $R^{2b}$ is hydrogen and the other is a $C_{1-6}$ alkyl group, $C_{1-6}$ alkoxy group, or halogen atom, or a salt thereof.

[18] The compound according to [16] wherein both $R^{2a}$ and $R^{2b}$ are $C_{1-6}$ alkyl groups, or a salt thereof.

[19] A compound represented by the following general formula (Ia):

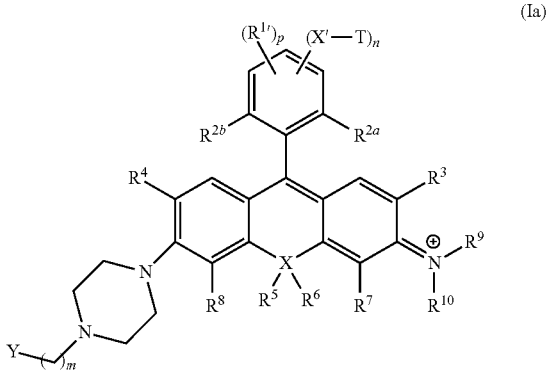

wherein, $R^3$ and $R^4$ are, each independently, a hydrogen atom, $C_{1-6}$ alkyl group, or halogen atom;

$R^5$ and $R^6$ are, when present, each independently, a $C_{1-6}$ alkyl group or aryl group, here, when X is an oxygen atom, $R^5$ and $R^6$ are not present, when X is a phosphorus atom, one of —$R^5$ and —$R^6$ may be =O;

$R^7$ and $R^8$ are, each independently, a hydrogen atom, $C_{1-6}$ alkyl group, or halogen atom;

$R^9$ and $R^{10}$ are, each independently, a hydrogen atom or $C_{1-6}$ alkyl group, $R^9$ or $R^{10}$, together with $R^3$ or $R^7$, may form a five- to seven-membered heterocyclyl or heteroaryl including the nitrogen atoms to which $R^9$ or $R^{10}$ is bonded, may also contain from one to three hetero atoms selected from the group consisting of an oxygen atom, nitrogen atom, and sulfur atom as ring members, and the heterocyclyl or heteroaryl may also be substituted by $C_{1-6}$ alkyl, $C_{2-6}$ alkenyl, or $C_{2-6}$ alkynyl, $C_{6-10}$ aralkyl group, or $C_{6-10}$ alkyl-substituted alkenyl group;

Y is a substituted or unsubstituted aryl group or heteroaryl group;

X is a silicon atom, oxygen atom, carbon atom, phosphorus atom, or germanium atom;

m is an integer of 0-6;

X' is a structure after a functional group capable of introducing a label site or target accumulation site has been bonded with T;

T is a crosslinking group; the crosslinking group may have a functional group capable of introducing a label site or target accumulation site or a functional group capable of bonding with a label site or target accumulation site at one or both ends;

$R^{1'}$ are hydrogen or the same or different monovalent substituents;

(i) $R^{2a}$ and $R^{2b}$ are, each independently, hydrogen or a monovalent substituent, but, $R^{2a}$ and $R^{2b}$ are not both hydrogen, or (ii) one of $R^{2a}$ and $R^{2b}$ is X'-T and the other of $R^{2a}$ and $R^{2b}$ is a monovalent substituent;

n is an integer of 0-2, p is an integer of 1-3, n+p=3; here, when n is 0, one of $R^{2a}$ and $R^{2b}$ is X'-T and the other is a monovalent substituent;

or a salt thereof.

[20] The compound according to [19] represented by the following general formula (IIa):

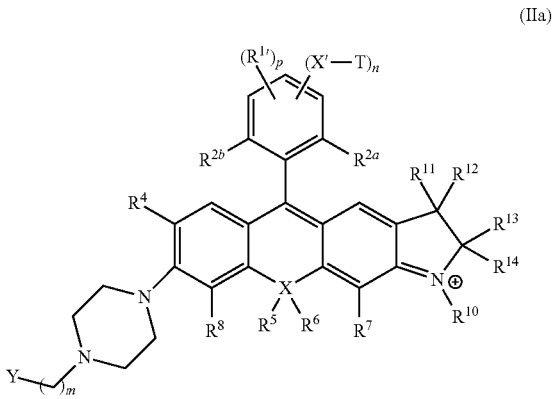

wherein, $R^4$-$R^8$, $R^{10}$, X, Y, and m are as defined in general formula (Ia);

$R^{11}$-$R^{14}$ are, each independently, a hydrogen atom, $C_{1-6}$ alkyl group, or halogen atom;

X', T, $R^{1'}$, $R^{2a}$-$R^{2b}$, n, and p are as defined in general formula (Ia)), or a salt thereof.

[21] The compound according to [19] or [20] wherein —X'-T is selected from the following, or a salt thereof.

(a) 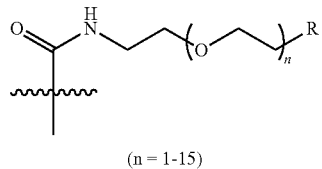

(n = 1-15)

(b) 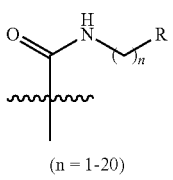

(n = 1-20)

(c) 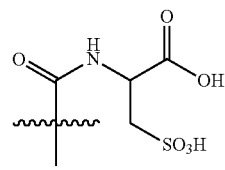

(d) 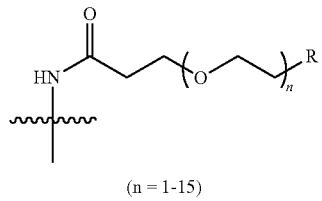

(n = 1-15)

(e) 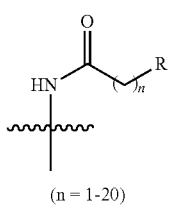

(n = 1-20)

R = COOH, NH$_2$, C≡CH

[22] A compound represented by the following general formula (Ib):

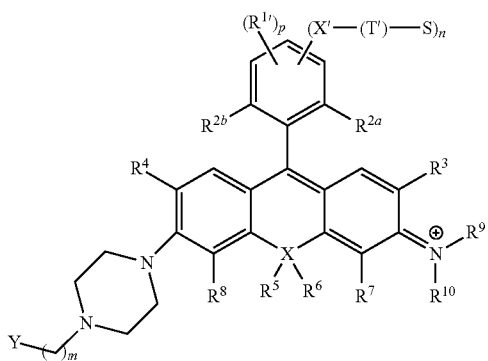

(Ib)

wherein,
$R^3$ and $R^4$ are, each independently, a hydrogen atom, $C_{1-6}$ alkyl group, or halogen atom;
$R^5$ and $R^6$ are, when present, each independently, a $C_{1-6}$ alkyl group or aryl group,
here, when X is an oxygen atom, $R^5$ and $R^6$ are not present,
when X is a phosphorus atom, one of —$R^5$ and —$R^6$ may be =O;
$R^7$ and $R^8$ are, each independently, a hydrogen atom, $C_{1-6}$ alkyl group, or halogen atom;
$R^9$ and $R^{10}$ are, each independently, a hydrogen atom or $C_{1-6}$ alkyl group,
$R^9$ or $R^{10}$, together with $R^3$ or $R^7$, may form a five- to seven-membered heterocyclyl or heteroaryl including the nitrogen atoms to which $R^9$ or $R^{10}$ is bonded, may also contain from one to three hetero atoms selected from the group consisting of an oxygen atom, nitrogen atom, and sulfur atom as ring members, and the heterocyclyl or heteroaryl may also be substituted by $C_{1-6}$ alkyl, $C_{2-6}$ alkenyl, or $C_{2-6}$ alkynyl, $C_{6-10}$ aralkyl group, or $C_{6-10}$ alkyl-substituted alkenyl group;
Y is a substituted or unsubstituted aryl group or heteroaryl group;
X is a silicon atom, oxygen atom, carbon atom, phosphorus atom, or germanium atom;
m is an integer of 0-6;
X' is a structure after a functional group capable of introducing a biopolymer label site has been bonded with T;
T', when present, is a structure after a crosslinking group has bonded with S;
S is a label site or target accumulation site;
$R^{1'}$ are hydrogen or the same or different monovalent substituents;
$R^{2a}$ and $R^{2b}$
(i) are, each independently, hydrogen or a monovalent substituent, but, $R^{2a}$ and $R^{2b}$ are not both hydrogen, or
(ii) one of $R^{2a}$ and $R^{2b}$ is X'-(T')-S and the other of $R^{2a}$ and $R^{2b}$ is a monovalent substituent;
n is an integer of 0-2, p is an integer of 1-3, n+p=3; here, when n is 0, one of $R^{2a}$ and $R^{2b}$ is X'-(T')-S and the other is a monovalent substituent), or a salt thereof.

[23] The compound according to [23] represented by the following general formula (IIb):

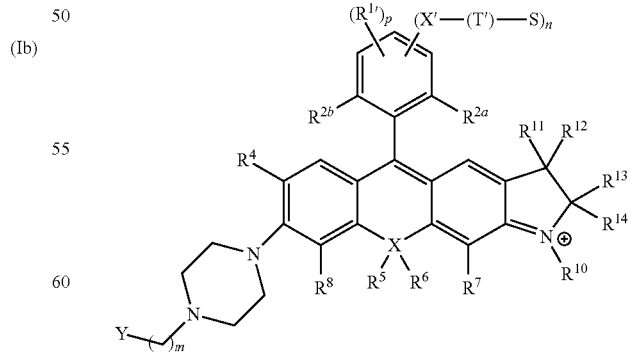

(IIb)

wherein,
$R^4$-$R^8$, $R^{10}$, X, Y, and m are as defined in general formula (Ib);

$R^{11}$-$R^{14}$ are, each independently, a hydrogen atom, $C_{1-6}$ alkyl group, or halogen atom;

X', T', $R^{1\prime}$, S, $R^{2a}$-$R^{2b}$, 6n, and p are as defined in general formula (Ib).), or a salt thereof.

[24] The compound according to [22] or [23] wherein —S is selected from the following, or a salt thereof.

(a)

X = H or SO₃H (b)

(c)

(d)

X = H or SO₃H (e)

(f)

(g)

(h)

X = Cl, Br, I (i)

(j)

(k)

[25] A fluorescent probe including a compound according to any one of [1]-[24], or a salt thereof.

[26] A method for measuring an acidic region within a cell, said method comprising;

(a) a step for introducing a compound according to any one of [1]-[24] or a salt thereof into a cell and (b) a step for measuring the fluorescence emitted within the cell by the compound or salt thereof.

[27] The method according to [26] that measures an acidic region in which an intracellular acidic organelle is present.

The present invention makes it possible to provide a pH probe having a high fluorescence quantum yield and high resistance to photobleaching suitable for visualization of pH environments within cells of weakly acidic environments. It also makes it possible to provide a pH probe group suitable for visualization of various pH environments within cells, such as weakly basic, neutral, and weakly acidic environments in which the pKa can be adjusted, as in lowered or raised, by also introducing electron withdrawing groups and electron donating groups onto the electron withdrawing group introduced onto the piperazine ring amino group.

DETAILED DESCRIPTION

Figure 1:
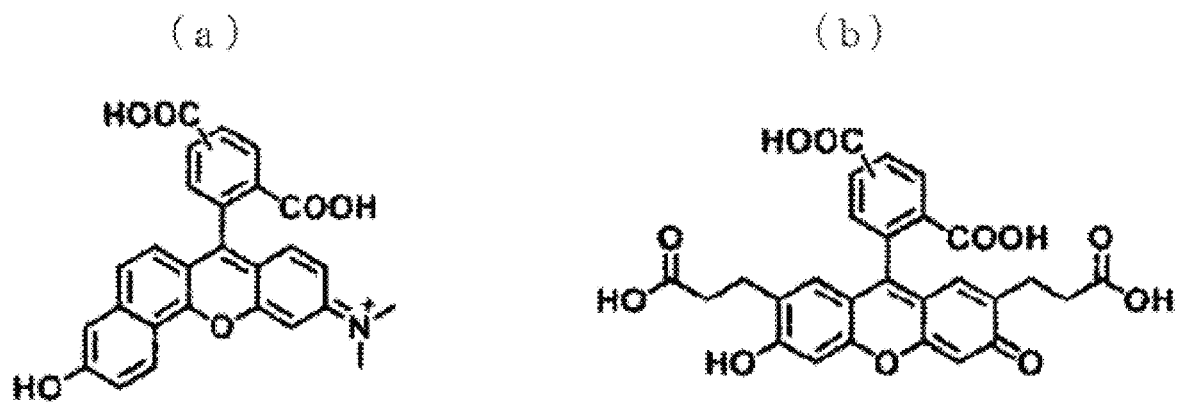
FIG. 1 is structural formulas of widely used pH probes.

In the present specification, an "alkyl group" or alkyl moiety of a substituent including an alkyl moiety (such as an alkoxy group), when not mentioned in particular, means a $C_{1-6}$, preferably $C_{1-4}$, more preferably $C_{1-3}$, linear, branched, cyclic, or combination thereof alkyl group. More specific examples include a methyl group, ethyl group, n-propyl group, isopropyl group, cyclopropyl group, n-butyl group, sec-butyl group, isobutyl group, tert-butyl group, cyclopropylmethyl group, n-pentyl group, n-hexyl group, and the like as alkyl groups.

When "halogen atom" is stated in the present specification, it may be any of a fluorine atom, chlorine atom, bromine atom, or iodine atom, preferably a fluorine atom, chlorine atom, or bromine atom.

One embodiment of the present invention is a compound represented by the following general formula (I) or a salt thereof (also referred to hereinafter as "embodiment 1").

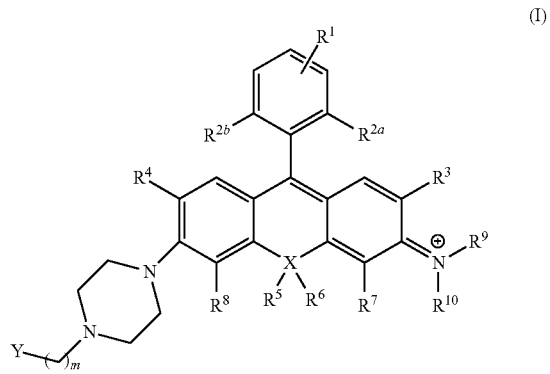

In general formula (I), $R^1$ represents a hydrogen atom or from one to three of the same or different monovalent substituents present on the benzene ring. Here, $R^1$ are introduced at three positions on the benzene ring other than positions substituted by $R^{2a}$ and $R^{2b}$. When $R^1$ represents monovalent substituents present on the benzene ring, one or two of the same or different substituents are preferably present on the benzene ring. When $R^1$ represents one or more monovalent substituents, the substituents can be substituted at any positions on the benzene ring. Preferably, $R^1$ represents hydrogen atoms (i.e., all $R^1$ are hydrogen atoms) or when one substituent is present (i.e., one $R^1$ is a monovalent substituent and the others are hydrogen atoms).

The type of monovalent substituent represented by $R^1$ is not particularly restricted, but monovalent substituents are preferably selected from the group consisting of a $C_{1-6}$ alkyl group, $C_{1-6}$ alkenyl group, $C_{1-6}$ alkynyl group, $C_{1-6}$ alkoxy group, hydroxyl group, carboxyl group, sulfonyl group, alkoxycarbonyl group, halogen atom, or amino group. These monovalent substituents may also have one or more arbitrary substituents. For example, one or more halogen atoms, carboxy groups, sulfonyl groups, hydroxyl groups, amino groups, alkoxy groups, and the like may be present in alkyl groups represented by $R^1$, and alkyl groups represented by $R^1$ may be alkyl halide groups, hydroxyalkyl groups, carboxyalkyl groups, aminoalkyl groups, or the like. One or more alkyl groups may also be present in amino groups represented by $R^1$, and amino groups represented by $R^1$ may be monoalkylamino groups or dialkylamino groups. In addition, carboxy-substituted alkoxy groups, alkoxycarbonyl-substituted alkoxy groups, and the like can be given as examples of when alkoxy groups represented by $R^1$ have substituents; more specific examples include a 4-carboxybutoxy group, 4-acetoxymethyloxycarbonylbutoxy group, and the like.

In one preferred aspect, $R^1$ is monovalent substituents such as $C_{1-6}$ alkyl groups, and the substituents are present at from position 3 to position 5 on the benzene ring.

In one embodiment of the present invention, at least one $R^1$ is a functional group capable of introducing a label site or target accumulation site (also referred to as a "biopolymer label site"). A functional group capable of introducing a label site or target accumulation site means a functional group capable of reacting with a label site or target accumulation site. Examples include a carboxyl group, alkyl group having a carboxyl group, ester group, alkyl ester group, amino group, amide group, alkylamino group, isothiocyanate group, sulfonyl chloride group, haloalkyl group, haloacetamide group, azide group, alkynyl group, and the like. Especially preferred are a carboxyl group, alkyl group having a carboxyl group, amino group, and amide group.

When at least one $R^1$ is a functional group capable of introducing a label site or target accumulation site, the other $R^1$ may be hydrogens or the abovementioned monovalent substituents ($C_{1-6}$ alkyl group, $C_{1-6}$ alkenyl group, $C_{1-6}$ alkynyl group, $C_{1-6}$ alkoxy group, hydroxyl group, carboxy group, sulfonyl group, alkoxycarbonyl group, halogen atom, or amino group).

In one preferred aspect, at least one $R^1$ is a functional group capable of introducing a label site or target accumulation site, and the functional group is present at from position 3 to position 5 on the benzene ring.

In a preferred aspect of the present invention, at least one $R^1$ is a functional group capable of introducing a label site or target accumulation site (most preferably a carboxyl group, alkyl group having a carboxyl group, amino group, or amide group), and the other $R^1$ are hydrogens.

In general formula (I), $R^{2a}$ and $R^{2b}$ each independently represent hydrogen or a monovalent substituent. However, $R^{2a}$ and $R^{2b}$ are not both hydrogen. The type of monovalent substituent represented by $R^{2a}$ and $R^{2b}$ is not particularly restricted. Like $R^1$, it is selected, for example, from the group consisting of a $C_{1-6}$ alkyl group, $C_{1-6}$ alkenyl group, $C_{1-6}$ alkynyl group, $C_{1-6}$ alkoxy group, hydroxyl group, carboxy group, sulfonyl group, alkoxycarbonyl group, halogen atom, or amino group.

In one preferred embodiment of the present invention, the monovalent substituent in $R^{2a}$ and $R^{2b}$ is a $C_{1-6}$ alkyl group, $C_{1-6}$ alkoxy group, or halogen atom.

In another preferred embodiment of the present invention, one of $R^{2a}$ and $R^{2b}$ is hydrogen and the other is a $C_{1-6}$ alkyl group, $C_{1-6}$ alkoxy group, or halogen atom.

In yet another preferred embodiment of the present invention, both $R^{2a}$ and $R^{2b}$ are $C_{1-6}$ alkyl groups. Though not intending to be bound by theory, this is because the stability of the probe in solution can be improved when both $R^{2a}$ and $R^{2b}$ are $C_{1-6}$ alkyl groups.

The monovalent substituent represented by $R^{2a}$ and $R^{2b}$ may also be a functional group capable of introducing a label site or target accumulation site. Examples of functional groups capable of introducing a label site or target accumulation site include a carboxyl group, alkyl group having a carboxyl group, ester group, alkyl ester group, amino group, amide group, alkylamino group, isothiocyanate group, sulfonyl chloride group, haloalkyl group, haloacetamide group, azide group, alkynyl group, and the like. Especially preferred are a carboxyl group, alkyl group having a carboxyl group, amino group, and amide group.

In one embodiment of the present invention, one of $R^{2a}$ and $R^{2b}$ is a monovalent substituent described above (preferably a $C_{1-6}$ alkyl group, $C_{1-6}$ alkoxy group, or halogen atom), and the other is a functional group capable of introducing a label site or target accumulation site. In this case, at least one $R^1$ may be a functional group capable of introducing a label site or target accumulation site, all $R^1$ may be hydrogens, or at least one $R^1$ may be a monovalent substituent such as a $C_{1-6}$ alkyl group and the remaining $R^1$ may be hydrogens.

In general formula (I), $R^3$ and $R^4$ each independently represent a hydrogen atom, $C_{1-6}$ alkyl group, or halogen atom. When $R^3$ and $R^4$ represent alkyl groups, one or more halogen atoms, carboxy groups, sulfonyl groups, hydroxyl groups, amino groups, alkoxy groups, or the like may be present in the alkyl group. For example, the alkyl group represented by $R^3$ or $R^4$ may be an alkyl halide group, hydroxyalkyl group, carboxyalkyl group, or the like. $R^3$ and $R^4$ each independently are preferably a hydrogen atom or halogen atom. It is more preferred when both $R^3$ and $R^4$ are hydrogen atoms or when both $R^3$ and $R^4$ are fluorine atoms or chlorine atoms.

In general formula (I), $R^5$ and $R^6$, when present, each independently represent a $C_{1-6}$ alkyl group or aryl group. It is preferred, however, that $R^5$ and $R^6$ each independently are $C_{1-3}$ alkyl groups, and more preferred that both $R^5$ and $R^6$ are methyl groups. One or more halogen atoms, carboxy groups, sulfonyl groups, hydroxyl groups, amino groups, alkoxy groups, or the like may be present in alkyl groups represented by $R^5$ and $R^6$. For example, the alkyl groups represented by $R^5$ and $R^6$ may be an alkyl halide group, hydroxyalkyl group, carboxyalkyl group, or the like. When $R^5$ or $R^6$ represents an aryl group, the aryl group may be a monocyclic aromatic group or a condensed aromatic group; and the aryl ring may include one or more ring member heteroatoms (such as a nitrogen atom, oxygen atom, or sulfur atom). A phenyl group is preferred as the aryl group. One or more substituents may be present on the aryl ring. For example, one or more halogen atoms, carboxy groups, sulfonyl groups, hydroxyl groups, amino groups, alkoxy groups, or the like may be present as substituents.

When X, which will be described later, is an oxygen atom, $R^5$ and $R^6$ are not present.

When X is a phosphorus atom, one of —$R^5$ and —$R^6$ may be =O. In a preferred aspect of when X is a phosphorus atom, one of —$R^5$ and —$R^6$ is =O and the other represents a $C_{1-6}$ alkyl group or aryl group.

In general formula (I), $R^7$ and $R^8$ each independently represent a hydrogen atom, $C_{1-6}$ alkyl group, or halogen atom, the same as explained for $R^3$ and $R^4$. It is preferred that $R^7$ and $R^8$ are both hydrogen atoms, that both are chlorine atoms, or that both are fluorine atoms.

In general formula (I), $R^9$ and $R^{10}$ each independently represent a hydrogen atom or $C_{1-6}$ alkyl group.

In addition, $R^9$ or $R^{10}$, together with $R^3$ or $R^7$, may form a five- to seven-membered heterocyclyl or heteroaryl including the nitrogen atoms to which $R^9$ or $R^{10}$ is bonded, may also contain from one to three heteroatoms selected from the group consisting of an oxygen atom, nitrogen atom, or sulfur atom as ring members, and the heterocyclyl or heteroaryl may also be substituted by $C_{1-6}$ alkyl, $C_{2-6}$ alkenyl, or $C_{2-6}$ alkynyl, $C_{6-10}$ aralkyl group (benzyl group, phenethyl group, or the like), or $C_{6-10}$ alkyl-substituted alkenyl group. Examples of the heterocyclyl or heteroaryl formed in this way include, but are not limited to, pyrrolidine, piperidine, hexamethyleneimine, pyrrole, imidazole, pyrazole, oxazole, thiazole, and the like.

In general formula (I), Y represents a substituted or unsubstituted aryl group or heteroaryl group. In the present invention, the pKa of the piperazine ring amino group can be changed by introducing an aryl group or heteroaryl group, which is an electron-withdrawing group, onto the piperazine ring amino group, thereby making it possible to adjust the pKa of the pH probe easily.

Examples of aryl groups include a phenyl group and naphthyl group; a phenyl group is preferred. Examples of heteroaryl groups include a pyridyl group, pyrazyl group, pyrimidyl group, pyridazyl group, indolyl group, benzofuranyl group, benzothienyl group, benzothiazolyl group, pyrrolyl group, furanyl group, thienyl group, imidazolyl group, thiazolyl group; a pyridyl group is preferred.

In addition, in the present invention, further adjustment as in raising or lowering the pKa is possible by introducing additional electron withdrawing groups or electron donating groups into the aryl group or heteroaryl group introduced onto the piperazine ring amino group.

As for substituents introduced into the aryl group or heteroaryl group, examples of electron withdrawing groups include a nitro group, sulfonyl group, carbonyl group, halogen atom (fluorine atom, chlorine atom, bromine atom, or iodine atom), $C_{1-6}$ alkoxy group, and the like. A fluorine atom and sulfonyl group are preferred. The aryl group or heteroaryl group can have two or more of the above electron withdrawing groups; these electron withdrawing groups may be the same or different.

Examples of electron donating groups include an amino group, methoxy group, and $C_{1-6}$ alkyl groups. A t-butyl group, sec-butyl group, n-butyl group, iso-propyl group, n-propyl group, ethyl group, methyl group, amino group, and methoxy group are preferred. The aryl group or heteroaryl group can have two or more of the above electron donating groups; these electron donating groups may be the same or different.

In general formula (I), m is an integer of 0-6. In general formula (I), m is preferably 0 or 1 to obtain an effective electron withdrawing effect of the aryl group or heteroaryl group introduced as Y.

A preferred embodiment of the present invention is when Y is a substituted or unsubstituted phenyl group and m is 1, i.e., an unsubstituted benzyl group is introduced into the piperazine ring amino group.

A preferred aspect of the present invention is a compound in which Y in general formula (I) is a phenyl group substituted by a fluorine atom and m is 1, or a salt thereof.

A preferred aspect of the present invention is a compound in which Y in general formula (I) is a phenyl group substituted by a sulfonyl group and m is 1, or a salt thereof.

A preferred aspect of the present invention is a compound in which Y in general formula (I) is a phenyl group substituted by two sulfonyl groups and m is 1, or a salt thereof.

In general formula (I), X represents a silicon atom, oxygen atom, carbon atom, phosphorus atom, or germanium atom. However, a silicon atom or germanium atom is preferred, and a silicon atom is especially preferred.

One aspect of embodiment 1 of the present invention is a compound represented by the following general formula (II):

(II)

or a salt thereof.

In general formula (II), $R^1$-$R^{2b}$, $R^4$-$R^8$, $R^{10}$, X, Y, and m are as described above in general formula (I).

In general formula (II), $R^{11}$-$R^{14}$ each independently represent a hydrogen atom, $C_{1-6}$ alkyl group, or halogen atom.

In one preferred embodiment of the present invention, $R^{11}$-$R^{14}$ each independently are a hydrogen atom or $C_{1-6}$ alkyl group (preferably a methyl group or ethyl group).

In one preferred embodiment of the present invention, $R^{11}$-$R^{14}$ are all hydrogen atoms.

The following compounds can be given as non-limiting examples of compounds of general formula (I) or (II) of the present invention.

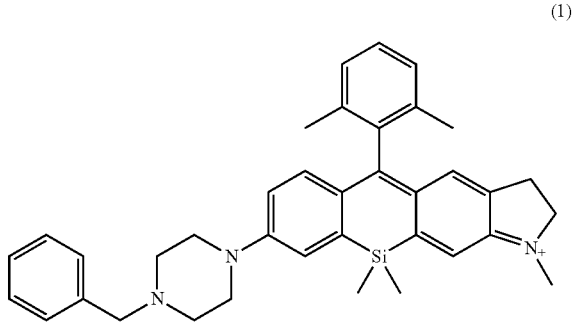

(1)

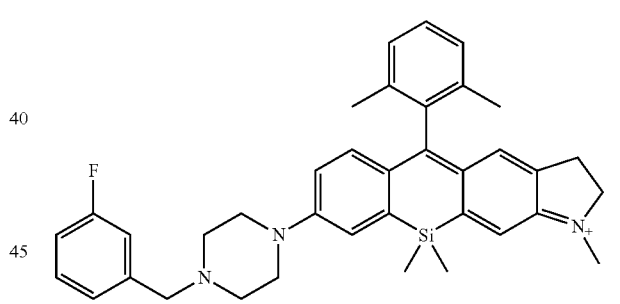

(2)

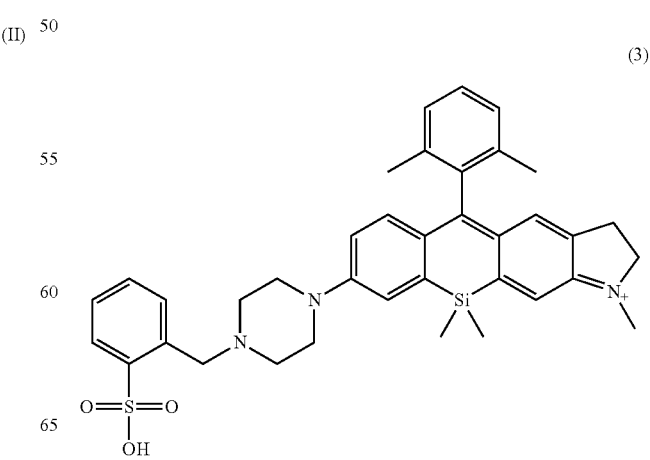

(3)

-continued

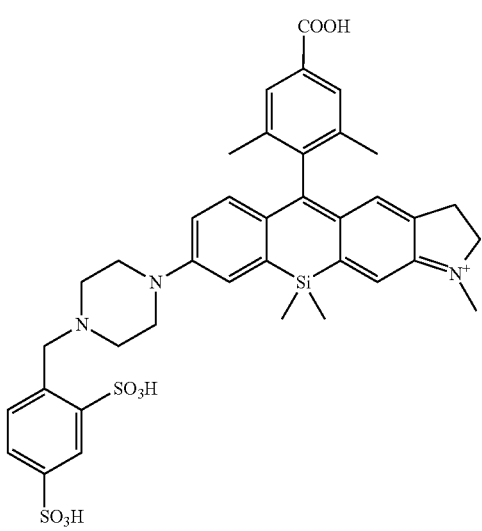

(4)

Compounds of the present invention represented by general formulas (I) and (II) can exist as acid addition salts or base addition salts. Examples of acid addition salts can include mineral acid salts such as a hydrochloride, sulfate, nitrate, and the like or organic acid salts such as a methanesulfonate, p-toluenesulfonate, oxalate, citrate, tartrate, and the like. Examples of base addition salts can include metal salts such as a sodium salt, potassium salt, calcium salt, magnesium salt, and the like, an ammonium salt, or an organic amine salt such as a triethylamine salt, and the like. In addition to these, there are also cases in which a salt is formed with an amino acid such as glycine. Compounds of the present invention or salts thereof can also sometimes exist as hydrates or solvates. These substances are also within the scope of the present invention.

Compounds of the present invention represented by general formulas (I) and (II) sometimes have one or more asymmetrical carbons, depending on the types of substituents. Stereoisomers such as optically active compounds based on one or more asymmetrical carbons and diastereomers based on two or more asymmetrical carbons as well as any mixtures of stereoisomers, racemates, and the like are all encompassed within the scope of the present invention.

Typical compound production methods for compounds represented by general formulas (I) and (II) of the present invention are shown concretely in the examples in this specification. Therefore, one skilled in the art can produce compounds of the present invention represented by general formulas (I) and (II) by appropriately selecting the reaction raw materials, reaction conditions, reaction reagents, and the like and by modifying or changing these methods as needed based on these explanations.

Another embodiment of the present invention is a compound in which at least one $R^1$ in general formula (I) or (II) is a functional group capable of introducing a label site or target accumulation site and the functional group is bonded with a crosslinking group, or a salt thereof (also referred to hereinafter as "embodiment 2").

Here, a carbonyl group, alkylcarbonyl group, ester group, alkyl ester group, amino group, alkylamino group, amide group, isothiocyanate group, sulfonyl chloride group, haloalkyl group, haloacetamide group, azide group, alkynyl group, and the like are preferred as the functional group capable of introducing a label site or target accumulation site; a carbonyl group or alkylcarbonyl group is especially preferred.

In addition, the crosslinking group may be any crosslinking group as long as it acts as a spacer to couple a functional group capable of introducing a label site or target accumulation site and a label site or target accumulation site. Examples include, but are not limited to, a substituted or unsubstituted hydrocarbon group (an alkane, alkene, alkyne, cycloalkane, aromatic hydrocarbon, and the like), ethylene glycol group, diethylene glycol group, triethylene glycol group, polyethylene glycol group, and the like, alkyl cysteinate, and heterocyclic group (for example, a piperidinyl group and the like), and the like. The crosslinking group may have a functional group capable of introducing a label site or target accumulation site or a functional group capable of bonding with a label site or target accumulation site at one or both ends. Examples of such functional groups include an amino group, carbonyl group, carboxyl group, amide group, propargyl group, and the like.

One aspect of embodiment 2 is a compound represented by the following general formula (Ia) or a salt thereof.

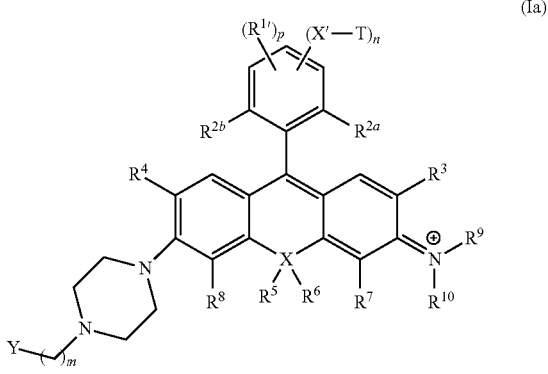

(Ia)

In general formula (Ia), $R^3$-$R^{10}$, X, Y, and m are as defined in general formula (I).

In general formula (Ia), X' is a structure after the functional group capable of introducing a label site or target accumulation site has bonded with T; T is the above crosslinking group.

The crosslinking group may have a functional group capable of introducing a label site or target accumulation site or a functional group capable of bonding with a label site or target accumulation site at one or both ends. Examples of such functional groups include an amino group, carbonyl group, carboxyl group, amide group, propargyl group, and the like.

$R^{1'}$ are hydrogens or the same or different monovalent substituents defined as $R^1$ in general formula (I). The details are explained for compounds of general formula (I).

$R^{1'}$ is preferably hydrogens.

In general formula (Ia), $R^{2a}$ and $R^{2b}$ each independently represent a hydrogen or monovalent substituent; however, $R^{2a}$ and $R^{2b}$ are not both hydrogen.

In addition, one of $R^{2a}$ and $R^{2b}$ can be X'-T. In this case, the other of $R^{2a}$ and $R^{2b}$ is a monovalent substituent (preferably a $C_{1-6}$ alkyl group, $C_{1-6}$ alkoxy group, or halogen atom).

In general formula (Ia), n is an integer of 0-2, p is an integer of 1-3, and n+p=3.

Here, when n is 0, one of $R^{2a}$ and $R^{2b}$ is X'-T and the other is a monovalent substituent (preferably a $C_{1-6}$ alkyl group, $C_{1-6}$ alkoxy group, or halogen atom).

As above, —(X'-T) in general formula (Ia) can be introduced at any of positions 2-6 of the benzene ring.

In a preferred aspect represented by general formula (Ia), n is 1 and p is 2. In this case, $R^{1\prime}$ may be the same or different. In this case, one of $R^{2a}$ and $R^{2b}$ may be X'-T. In this case, the other of $R^{2a}$ and $R^{2b}$ is a monovalent substituent (preferably a $C_{1-6}$ alkyl group, $C_{1-6}$ alkoxy group, or halogen atom).

Another aspect of embodiment 2 is a compound represented by the following general formula (IIa) or a salt thereof.

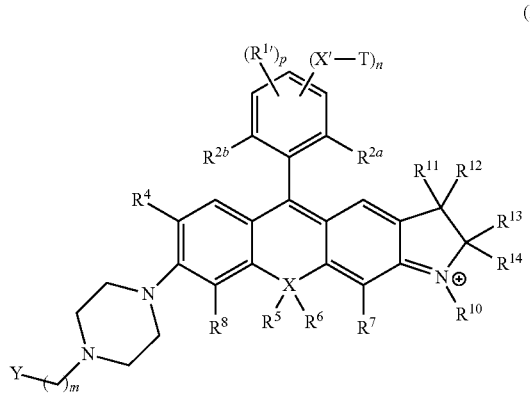

(IIa)

In general formula (IIa), $R^4$-$R^8$, $R^{10}$, X, Y, and m are as defined in general formula (I). $R^{11}$-$R^{14}$ each independently represent a hydrogen atom, alkyl group, or halogen atom. X', T, $R^{1\prime}$, $R^{2a}$-$R^{2b}$, n, and p are as defined in general formula (Ia).

In a preferred aspect represented by general formula (IIa), n is 1 and p is 2. In this case, $R^{1\prime}$ may be the same or different. In this case, one of $R^{2a}$ and $R^{2b}$ may be X'-T. In this case, the other of $R^{2a}$ and $R^{2b}$ is a monovalent substituent (preferably a $C_{1-6}$ alkyl group, $C_{1-6}$ alkoxy group, or halogen atom).

In one preferred aspect of embodiment 2, —X'-T in general formula (Ia) or (IIa) is selected from the following.

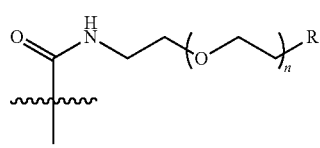

(a)

(n = 1-15)

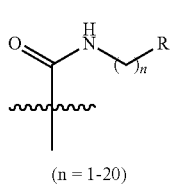

(b)

(n = 1-20)

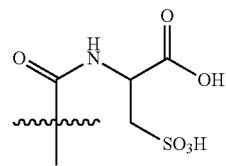

(c)

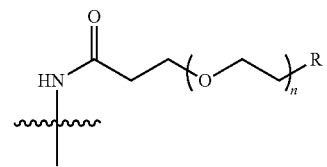

(d)

(n = 1-15)

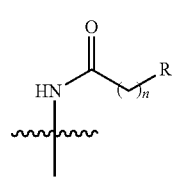

(e)

(n = 1-20)

R = COOH, $NH_2$, C≡CH

Another embodiment of the present invention is a compound in which at least one of $R^1$ in general formula (I) or (II) is a functional group capable of introducing a label site or target accumulation site, the functional group bonds with a crosslinking group, and the crosslinking group bonds with a label site or target accumulation site, or a salt thereof.

Another embodiment of the present invention is a compound in which at least one of $R^1$ in general formula (I) or (II) is a functional group capable of introducing a label site or target accumulation site, and the functional group bonds with a label site or target accumulation site without the intervention of a crosslinking group.

The above two embodiments are also collectively termed "embodiment 3."

The functional group capable of introducing a label site or target accumulation and the crosslinking group are as explained in embodiment 2.

Examples of a label site or target accumulation site include an N-hydroxysuccinimide ester, Halo tag ligand (for example, a 2-(2-((6-chlorohexyl)oxy)ethoxy)ethaneamino group), weakly basic amine, maleimide, isothiocyanate group, sulfonyl chloride group, haloalkyl group, haloacetamide group, amide group, azide group, alkynyl group, benzylguanine derivative or benzylcytosine derivative, and the like. The label site or target accumulation site also includes a polyethylene glycol group which may have a modifying group at one or both ends. Examples of the modifying group include an amino group, carbonyl group, carboxyl group, and the like. Non-limiting examples of polyethylene glycol groups having a modifying group include 3-(2-(2-(2-aminoethoxy)ethoxy)ethoxy)propanoic acid.

Compounds or salts thereof included in embodiment 3 make it possible to visualize various phenomena involving intracellular acidic vesicles in real time because they have strong fluorescence in acidic environments, can label specific proteins and the like, and can be localized within acidic organelle cells. Furthermore, compounds in which a label site or target accumulation site has been introduced into part of a functional group capable of introducing a label site or target accumulation site, that is, compounds having both a functional group capable of introducing a label site or target accumulation site and a substituent having a label site or target accumulation site introduced, are also included in embodiment 3.

One aspect of embodiment 3 is a compound represented by the following general formula (Ib) or a salt thereof.

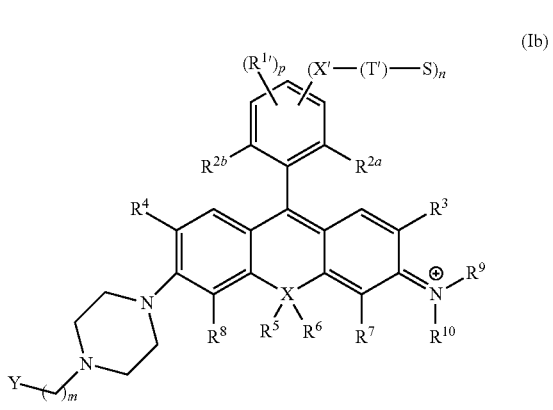

In general formula (Ib), $R^3$-$R^{10}$, X, Y, and m are as defined in general formula (I).

In formula (Ib), X' is a structure after the functional group capable of introducing a label site or target accumulation site has bonded with T, T', when present, is a structure after the crosslinking group has bonded with S, and S is a label site or target accumulation site.

In addition, $R^{1'}$ are hydrogens or the same or different monovalent substituents defined as $R^1$ of general formula (I). The details are as explained for compounds of general formula (I).

$R^{1'}$ are preferably hydrogens.

In general formula (Ib), $R^{2a}$ and $R^{2b}$ each independently represent a hydrogen or monovalent substituted; however, $R^{2a}$ and $R^{2b}$ are not both hydrogen.

In addition, one of $R^{2a}$ and $R^{2b}$ can be X'-(T')-S. In this case, the other of $R^{2a}$ and $R^{2b}$ is a monovalent substituent (preferably a $C_{1-6}$ alkyl group, $C_{1-6}$ alkoxy group, or halogen atom).

In general formula (Ib), n is an integer of 0-2, p is an integer of 1-3, and n+p=3.

Here, when n is 0, one of $R^{2a}$ and $R^{2b}$ is X'-(T')-S, and the other is a monovalent substituent (preferably a $C_{1-6}$ alkyl group, $C_{1-6}$ alkoxy group, or halogen atom).

As above, in general formula (Ib), —(X'-(T')-S) can be introduced to any of positions 2-6 of the benzene ring.

In a preferred aspect represented by general formula (Ib), n is 1 and p is 2. In this case, $R^{1'}$ may all be the same or different. In this case, one of $R^{2a}$ and $R^{2b}$ may be X'-(T')-S. In this case, the other of $R^{2a}$ and $R^{2b}$ is a monovalent substituent (preferably a $C_{1-6}$ alkyl group, $C_{1-6}$ alkoxy group, or halogen atom).

In general formula (Ib), T' may be present or absent (when absent, S bonds directly to X'). Here, it is usually preferred that T' be present since synthesis is simple when there is no crosslinking group, but the characteristics of the dye molecule can be changed by interaction with a protein surface.

In addition, the crosslinking group may have a functional group capable of introducing a label site or target accumulation site or a functional group capable of bonding with a label site or target accumulation site at one or both ends. Examples of such functional groups include an amino group, carbonyl group, carboxyl group, amide group, propargyl group, and the like.

Another aspect of embodiment 3 is a compound represented by the following general formula (IIb) or a salt thereof.

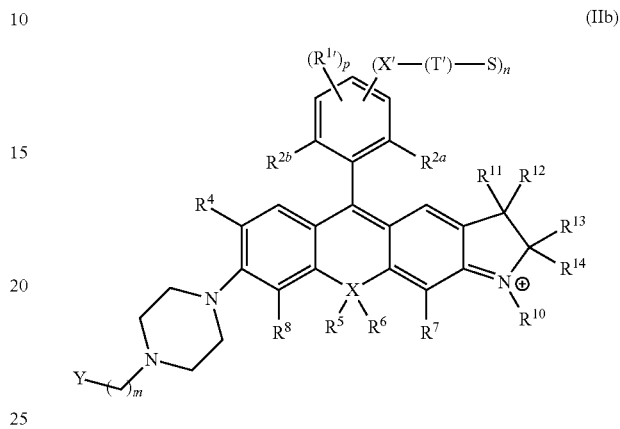

In general formula (IIb), $R^4$-$R^8$, $R^{10}$, X, Y, and m are as defined in general formula (I), $R^{11}$-$R^{14}$ each independently represent a hydrogen atom, $C_{1-6}$ alkyl group or halogen atom, and X', T', $R^{1'}$, S, n, and p are as defined in general formula (Ib).

In a preferred aspect of compounds represented by general formula (IIb), n is 1 and p is 2. In this case, $R^{1'}$ may be the same or different. In this case, one of $R^{2a}$ and $R^{2b}$ may be X'-(T')-S. In this case, the other of $R^{2a}$ and $R^{2b}$ is a monovalent substituent (preferably a $C_{1-6}$ alkyl group, $C_{1-6}$ alkoxy group, or halogen atom).

In one preferred aspect of embodiment 3, —S in general formula (Ib) or (IIb) is selected from the following.

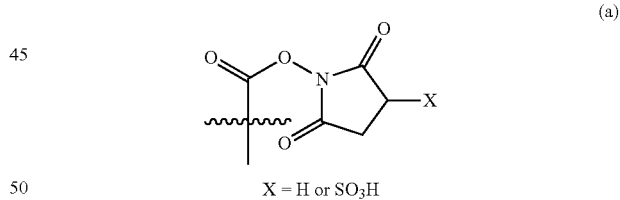

(a)

X = H or $SO_3H$

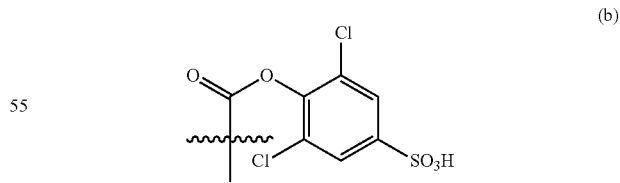

(b)

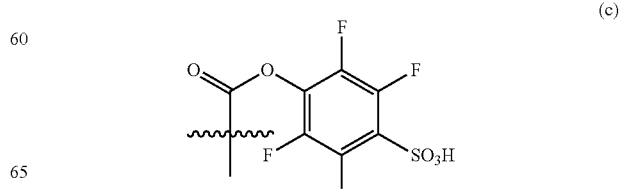

(c)

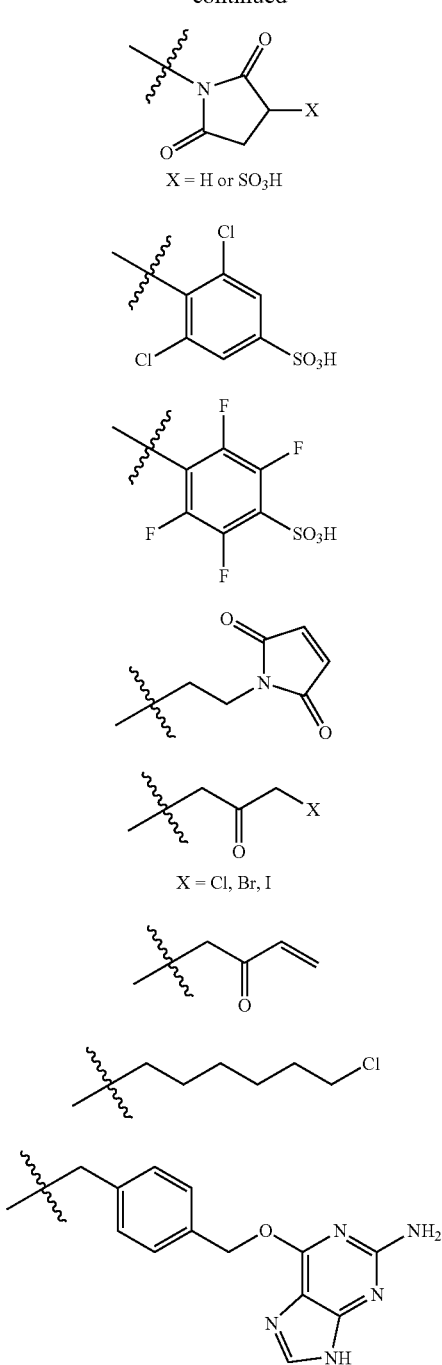

Compounds of embodiment 3, compounds of general formulas (Ib) and (IIb), make it possible to visualize various phenomena involving intracellular acidic vesicles in real time because they can label specific proteins and the like, and can be localized within acidic organelle cells. As a non-limiting example, when an N-hydroxysuccinimide ester as a label site or polyethylene glycol modified at the end by a carboxyl group or the like is introduced into the molecule, the fluorescent probe of the present invention can be localized in intracellular acidic vesicles by labeling by dextran, which is a sugar polymer. When a weakly basic amine is introduced into the molecule as a target accumulation site, the fluorescent probe of the present invention can be accumulated in acidic vesicles. In addition, when a Halo tag ligand is introduced as a label site, a label specific to the Halo tag becomes possible. Specifically, by expressing a protein (VAMP2-Halo tag) in which a Halo tag was fused to VAMP2, which is a synaptic vesicle marker, in nerve cells and adding a fluorescent probe of the present invention having a Halo tag ligand introduced thereto, it becomes possible for the fluorescent probe to specifically label the synaptic vesicles.

The compounds of embodiments 2 and 3 of the present invention can exist as acid addition salts or base addition salts. Examples of acid addition salts can include mineral acid salts such as a hydrochloride, sulfate, nitrate, and the like or organic acid salts such as a methanesulfonate, p-toluenesulfonate, oxalate, citrate, tartrate, and the like. Examples of base addition salts can include metal salts such as a sodium salt, potassium salt, calcium salt, magnesium salt, and the like, an ammonium salt, or an organic amine salt such as a triethylamine salt, and the like. In addition to these, there are also cases in which a salt is formed with an amino acid such as glycine. Compounds of the present invention or salts thereof can also sometimes exist as hydrates or solvates. These substances are also within the scope of the present invention.

Compounds of embodiments 2 and 3 of the present invention sometimes have one or more asymmetrical carbons, depending on the types of substituents. Stereoisomers such as optically active compounds based on one or more asymmetrical carbons and diastereomers based on two or more asymmetrical carbons as well as any mixtures of stereoisomers, racemates, and the like are all encompassed within the scope of the present invention.

Typical compound production methods for compounds of the present invention represented by general formulas (Ia), (IIa), (Ib), and (IIb) are shown concretely in the examples in this specification. Therefore, one skilled in the art can produce compounds of the present invention represented by general formulas (Ia), (IIa), (Ib), and (IIb) by appropriately selecting the reaction raw materials, reaction conditions, reaction reagents, and the like and by modifying or changing these methods as needed based on these explanations.

Another embodiment of the present invention is a fluorescent probe including a compound of general formula (I), (II), (Ia), (IIa), (Ib), or (IIb) or a salt thereof.

In addition, another embodiment of the present invention is a method for measuring an acidic region within a cell wherein the method includes (a) a step for introducing a compound of general formula (I), (II), (Ia), (IIa), (Ib), or (IIb) or a salt thereof into a cell and (b) a step for measuring the fluorescence emitted by the compound or salt thereof in the cell.

In addition, another aspect of the present invention is a method for measuring an acidic region present in an intracellular acidic organelle.

Yet another embodiment of the present invention is a method for monitoring the pH of the interior of a living cell that includes (a) a stage for bringing a cell into contact with a compound of general formula (I), (II), (Ia), (IIa), (Ib), or (IIb) or a salt thereof and forming a contacted cell, (b) a stage for incubating the contacted cell for the compound to penetrate the cell and forming a labeled cell, and (c) a stage for irradiating the labeled cell using a wavelength suited to the measurement of fluorescence, and thereby monitoring the pH of the interior of the cell.

Here, examples of the cell include normal cells, cancer cells, nerve cells, and the like.

Method Described in Section.

Yet another embodiment of the present invention is a method for detecting phagocytosis of a carrier molecule in a solution including (a) a stage for bonding a carrier molecule to a compound of general formula (I), (II), (Ia), (IIa), (Ib), or (IIb) or a salt thereof and forming a carrier conjugate, (b) a stage for bringing the carrier conjugate into contact with a cell and forming a contacted cell, (c) a stage for incubating the contacted cell and forming an incubated solution, (d) a stage for irradiating the incubated solution and forming an irradiated solution, and (e) a stage for detecting fluorescent emission from the irradiated solution, wherein the fluorescent emission represents phagocytosis of the carrier molecule.

Carrier molecules include amino acids, peptides, proteins, polysaccharides, nucleosides, nucleotides, oligonucleotides, nucleic acids, haptens, psoralen, drugs, hormones, lipids, lipid aggregates, synthetic polymers, polymer microparticles, biological cells, viruses, and combinations thereof.

In an exemplary embodiment, this carrier molecule is an amino acid (including an amino acid that is protected or substituted by a phosphate, carbohydrate, or $C_{1-22}$ carboxylic acid) or a polymer of amino acids (such as a peptide or protein). In a related embodiment, this carrier molecule includes at least five amino acids, more preferably 5-36 amino acids. Examples of peptides include, but are not limited to, neuropeptides, cytokines, toxins, protease substrates, and protein kinase substrates. Other exemplary peptides may function as organelle localization peptides, that is, peptides that target the conjugated compound for localization within a specific cellular substructure by a cellular transport mechanism. Preferred protein carrier molecules include enzymes, antibodies, lectins, glycoproteins, histones, albumins, lipoproteins, transferrins, avidin, streptavidin, protein A, protein G, phycobiliproteins, and other fluorescent proteins, hormones, toxins, and growth factors. Typically, this protein carrier molecule is an antibody, antibody fragment, avidin, streptavidin, toxin, lectin, growth factor, bacterial particle, or cell receptor binding partner.

Examples of nucleic acid polymer carrier molecules are single- or multi-stranded, natural or synthetic DNA or RNA oligonucleotides, or DNA/RNA hybrids, or those incorporating an unusual linker such as morpholine derivatized phosphates (AntiVirals, Inc., Corvallis Oreg.), or peptide nucleic acids (such as N-(2-aminoethyl)glycine units), where the nucleic acid contains fewer than 50 nucleotides, more typically fewer than 25 nucleotides.

In another exemplary embodiment, this carrier molecule includes a carbohydrate or a polyol that is typically a polysaccharide, such as dextran, Ficoll, heparin, glycogen, amylopectin, mannan, inulin, starch, agarose and cellulose, or is a polymer such as a poly(ethylene glycol). In a related embodiment, examples of the polysaccharide carrier molecule include dextran, agarose, or Ficoll.

In another exemplary embodiment, this carrier molecule includes a lipid (typically including 6-25 carbons), including glycolipids, phospholipids, and sphingolipids. Alternatively, this carrier molecule includes a lipid vesicle (such as a liposome) or is a lipoprotein (see below). Some lipophilic substituents are useful for facilitating transport of the conjugated dye into cells or cellular organelles.

EXAMPLES

The present invention is explained below through examples. The present invention, however, is not limited to these examples.

Example 1

(1) Synthesis of Synthesis Intermediate 1

A synthesis intermediate 1 (tert-butyl 4-(1,10,10-trimethyl-5-oxo-2,3,5,10-tetrahydro-1H-benzo[5,6]silino[3,2-f]indol-8-yl)piperazine-1-carboxylate (BocPiperaIndoSiXanthone)) was synthesized by scheme 1 below.

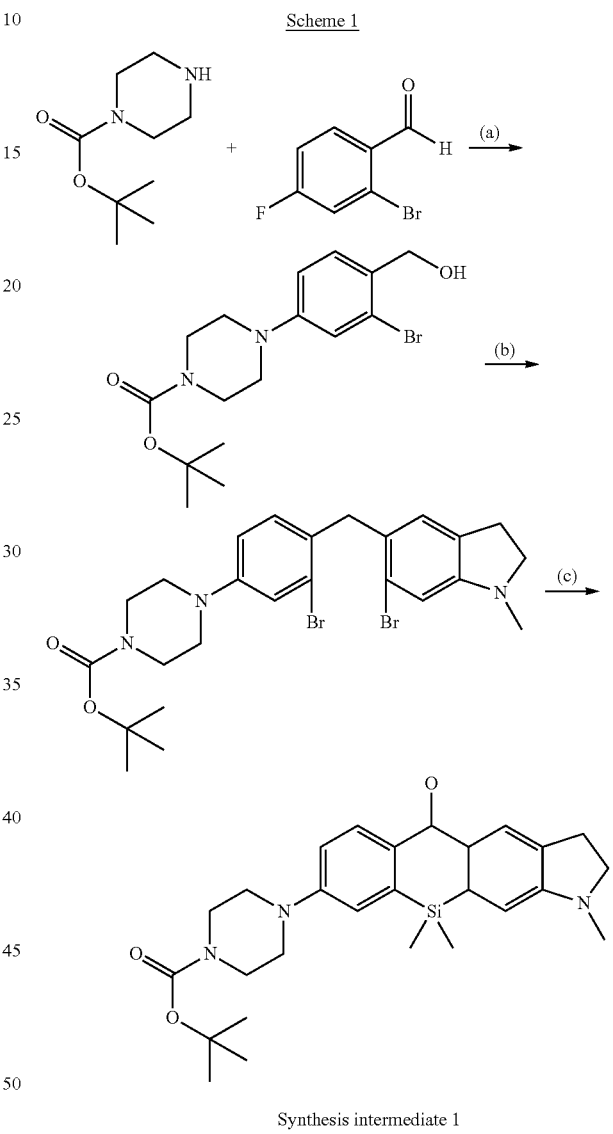

Synthesis intermediate 1

(a) (i) N-Boc-piperazine, $K_2CO_3$, DMF 100° C. (ii) $NaBH_4$, MeOH, r.t.
(b) $BF_3OEt_2$, 6-bromo-1-methylindoline, $CH_2Cl_2$, r.t.
(c) (i) sec-BuLi/THF, −78° C. (ii) $SiMe_2Cl_2$, −78° C.→r.t. (iii) $KMnO_4$, acetone, r.t.

(1) Step (a)

N-Boc-piperazine (2.41 g, 12.9 mmol) and 2-bromo-4-fluorobenzaldehyde (2.19 g, 10.8 mmol) were dissolved in DMF (30 mL). $K_2CO_3$ (2.24 g, 16.2 mmol) was added, and stirred for 18 hours at 100° C. After distilling off the solvent under reduced pressure, water was added to the residue. The mixture was extracted by dichloromethane and washed by brine. The organic layer was dried by $Na_2SO_4$, and the solvent was distilled off under reduced pressure. Methanol (30 mL) and sodium borohydride (494 mg, 13.0 mmol) were added, and stirred for three hours at room temperature. After distilling off the solvent under reduced pressure, water was added to the residue, and the mixture was extracted by dichloromethane. The organic layer was dried by $Na_2SO_4$, and the solvent was distilled off under reduced pressure. 2-Bromo-4-(1-Boc piperazyl)-benzyl alcohol (3.46 g, 9.33 mmol, yield 86%) was then obtained by purification by column chromatography (silica gel, ethyl acetate/n-hexane).

$^1$H NMR (300 MHz, $CDCl_3$): δ 1.48 (s, 9H), 2.02 (t, J=6.6 Hz, 1H), 3.13 (t, J=5.1 Hz, 4H), 3.56 (t, J=5.1 Hz, 4H), 4.66 (d, J=6.6 Hz, 2H), 6.85 (dd, J=8.1, 2.2 Hz, 1H), 7.08 (d, J=2.1 Hz, 1H), 7.32 (d, J=8.1 Hz, 1H); $^{13}$C NMR (75 MHz, $CDCl_3$) δ 28.40, 48.89, 64.77, 80.05, 115.35, 120.09, 123.85, 130.03, 130.87, 151.76, 154.64; HRMS (ESI$^+$) Calcd for [M+H]$^+$, 371.0970, Found, 371.0922 (−4.8 mmu).

(2) Step (b)

6-Bromo-1-methylindoline (23 mg, 0.108 mmol) and 2-bromo-4-(1-Boc piperazyl)-benzyl alcohol (41 mg, 0.110 mmol) were dissolved in dichloromethane (5 mL). $BF_3OEt_2$ (28 μL, 0.220 mmol) was added, and stirred for six hours at room temperature. Water was added to the reaction solution, and the mixture was extracted by dichloromethane. The organic layer was dried by $Na_2SO_4$, and the solvent was distilled off under reduced pressure. The residue was purified by column chromatography (silica gel, ethyl acetate/n-hexane), and 4-(3-bromo-4-((6-bromo-1-methylindolin-5-yl)methyl)phenyl)Boc piperazine (53 mg, 0.0937 mmol, yield 87%) was obtained.

$^1$H NMR (300 MHz, $CDCl_3$): δ 1.48 (s, 9H), 2.73 (s, 3H), 2.82 (t, J=8.1 Hz, 2H), 3.10 (t, J=5.1 Hz, 4H), 3.30 (t, J=8.1 Hz, 2H), 3.56 (t, J=5.1 Hz, 4H), 4.00 (s, 2H), 6.65 (s, 1H), 6.70 (s, 1H), 6.77 (dd, J=8.7, 2.1 Hz, 1H), 6.88 (d, J=8.7 Hz, 1H), 7.13 (d, J=2.1 Hz, 1H); $^{13}$C NMR (75 MHz, $CDCl_3$) δ 28.31, 28.40, 35.96, 40.38, 49.13, 56.22, 79.95, 110.81, 115.64, 120.25, 123.13, 125.36, 126.09, 127.47, 130.20, 130.77, 131.20, 150.52, 153.13, 154.65; HRMS (ESI$^+$) Calcd for [M+H]$^+$, 566.0841, Found, 566.0850 (+0.9 mmu).

(3) Step (c)

4-(3-Bromo-4-((6-bromo-1-methylindolin-5-yl)methyl) phenyl)Boc piperazine (1150 mg, 2.03 mmol) and dehydrated tetrahydrofuran (30 mL) were added to a dried, argon-purged flask. After cooling to −78° C., 1 M sec-butyllithium (4.26 mL, 4.16 mmol) was added, and stirred for 20 minutes. Dichlorodimethylsilane (257 μL, 2.23 mmol) dissolved in 10 mL of dehydrated tetrahydrofuran was slowly added at the same temperature. The mixture was returned to room temperature, and stirred for 13 hours. The reaction was stopped by 2N hydrochloric acid, and the mixture was neutralized by $NaHCO_3$. The mixture was extracted by dichloromethane, washed by brine, and the organic layer was dried by $Na_2SO_4$, and the solvent was distilled off under reduced pressure. Some of the by-products were then removed by column chromatography (silica gel, ethyl acetate/n-hexane). The residue was dissolved in acetone (30 mL), and cooled to 0° C. $KMnO_4$ (237 mg, 1.50 mmol) was added in small amounts over one hour, and stirred for one hour at the same temperature. Dichloromethane was added. After suction filtering using filter paper, water was added, and the mixture was extracted by dichloromethane and washed by brine. The organic layer was dried by $Na_2SO_4$, and the solvent was distilled off under reduced pressure. The residue was purified by column chromatography (silica gel, ethyl acetate/n-hexane), and tert-butyl 4-(1,10,10-trimethyl-5-oxo-2,3,5,10-tetrahydro-1H-benzo[5,6]silino[3,2-f]indol-8-yl)piperazine-1-carboxylate (52 mg, 0.109 mmol, yield 5%) was obtained.

$^1$H NMR (400 MHz, $CDCl_3$): δ 0.45 (s, 6H), 1.49 (s, 9H), 2.91 (s, 3H), 3.06 (t, J=9.0 Hz, 2H), 3.35 (t, J=5.0 Hz, 4H), 3.49 (t, J=9.0 Hz, 2H), 3.62 (t, J=5.0 Hz, 4H), 6.49 (s, 1H), 7.01-7.04 (m, 2H), 8.20 (s, 1H), 8.39 (d, J=8.0 Hz, 1H); $^{13}$C NMR (75 MHz, $CDCl_3$) δ −1.19, 27.88, 28.33, 34.36, 47.56, 54.63, 79.97, 107.74, 116.22, 117.61, 126.02, 130.95, 131.37, 132.20, 132.56, 140.21, 140.29, 151.98, 154.48, 154.91, 184.99; HRMS (ESI$^+$) Calcd for [M+H]$^+$, 478.2526, Found, 478.2483 (−4.3 mmu).

(2) Synthesis of Compound 1 from Synthesis Intermediate 1

Compound 1 (2,6-diMe BnPiperaIndoSiR) of the present invention was obtained from the synthesis intermediate 1 obtained as described above by scheme 2 below.

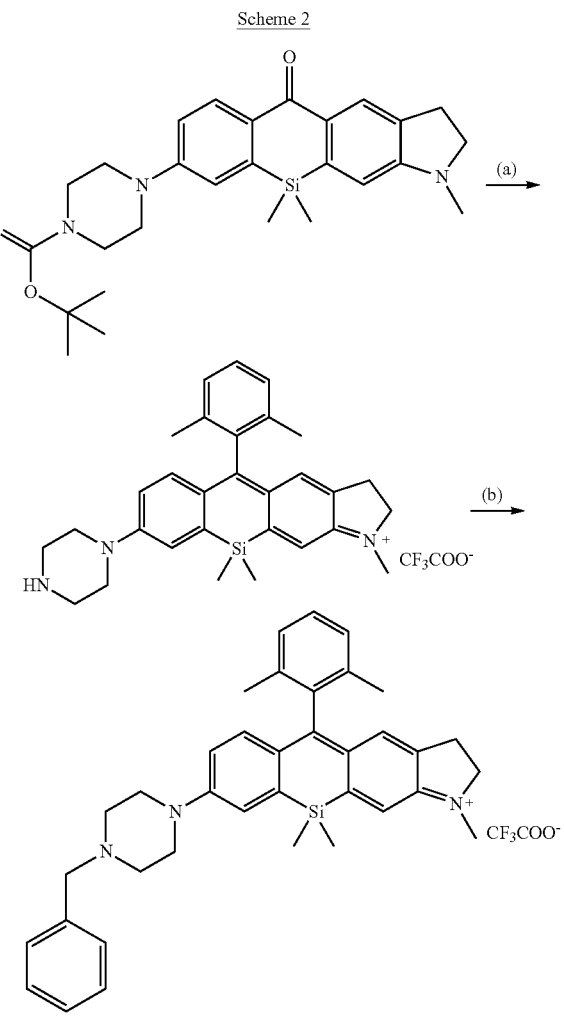

Scheme 2

Compound 1

(a) (i) 2,6-dimethylphenylmagnesium bromide, THF, reflux, (ii) 2N HCl aq., r.t. (iii) TFA, r.t. (b) (i) Benzaldehyde, $NaCNBH_3$, AcOH, MeOH (ii) p-Chloranil, $CH_2Cl_2$, r.t.

(1) Step (a)

Tert-butyl 4-(1,10,10-trimethyl-5-oxo-2,3,5,10-tetrahydro-1H-benzo[5,6]silino[3,2-f]indol-8-yl)piperazine-1-carboxylate (42 mg, 0.0879 mmol), dehydrated tetrahydrofuran (10 mL), and 2,6-dimethylphenyl magnesium bromide (2.64 mL, 2.64 mmol) were added to a dried, argon-purged flask, and heated under reflux for 3.5 hours. After the reaction solution had returned to room temperature, the reaction was stopped by 2N hydrochloric acid aqueous solution. After neutralizing by adding saturated sodium bicarbonate aqueous solution, the mixture was extracted by dichloromethane, the organic layer was dried by $Na_2SO_4$, and the solvent was distilled off under reduced pressure. Trifluoroacetic acid (5 mL) and dichloromethane (5 mL) were added to the residue, and stirred for three hours at room temperature. The residue was washed by hexane, then purified by HPLC (eluent, from 27% acetonitrile/0.1% trifluoroacetic acid/water (0 min) to 72% acetonitrile/0.1% TFA/water (20 min); flow rate=25.0 mL/min), and 2,6-diMe PiperaIndoSiR (3 mg, 5.17 μmol, yield 6%) was obtained.

HRMS (ESI$^+$) Calcd for [M]$^+$, 466.2679, Found, 466.2653 (−2.6 mmu).

(2) Step (b)

2,6-diMe PiperaIndoSiR (3 mg, 5.17 μmol) was dissolved in dichloromethane (5 mL) and methanol (1 mL). Benzaldehyde (1 μL, 9.91 μmol) and acetic acid (20 μL) were added, and stirred for 10 minutes at room temperature. Sodium cyanoborohydride (1.26 mg, 20 μmol) was added to the reaction solution, and stirred for 23 hours at room temperature. Water was added to the mixture, and the mixture was extracted by dichloromethane. The organic layer was dried by $Na_2SO_4$, and the solvent was distilled off under reduced pressure. Dichloromethane (10 mL) and p-chloranil (2 mg, 8.13 μmol) were added to the residue. After stirring for one hour at room temperature, the solvent was distilled off under reduced pressure. The residue was purified by HPLC (eluent, from 27% acetonitrile/0.1% trifluoroacetic acid/water (0 min) to 64% acetonitrile/0.1% TFA/water (20 min); flow rate=5.0 mL/min), and 2,6-diMe BnPiperaIndoSiR (1.5 mg, 2.24 μmol, yield 43%) was obtained. $^1$H NMR (400 MHz, $CD_3OD$): δ 0.49 (s, 6H), 0.60 (s, 3H), 1.90 (s, 6H), 2.51 (t, J=5.0 Hz, 4H), 2.91 (t, J=7.0 Hz, 2H), 3.25 (s, 3H), 3.49 (s, 2H), 3.54 (t, J=5.0 Hz, 4H), 3.85 (t, J=7.0 Hz, 4H), 6.58 (dd, J=8.6, 2.8 Hz, 1H), 6.72 (s, 1H), 6.89 (d, J=8.6 Hz, 1H), 6.97 (s, 1H), 7.10-7.12 (m, 3H), 7.18-7.28 (m, 6H); HRMS (ESI$^+$) Calcd for [M]$^+$, 556.3148, Found, 556.3134 (−1.4 mmu).

Example 2

(1) Synthesis of Compound 2

Compound 2 (SiRpH3) was synthesized by scheme 3 below.

Scheme 3

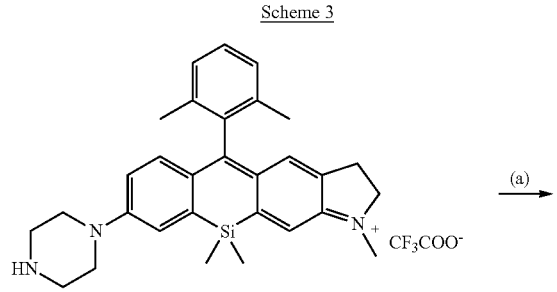

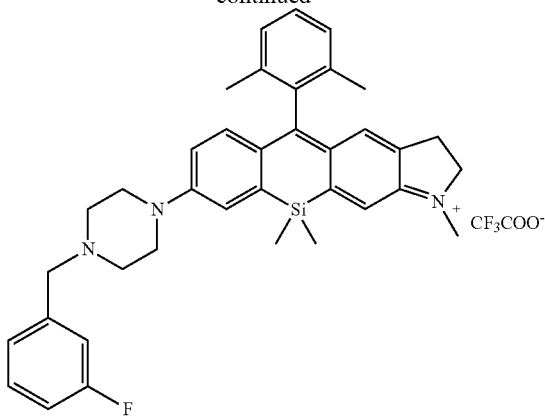

Compound 2

(a) (i) 3-fluorobenzaldehyde, $NaCNBH_3$, AcOH, MeOH, r.t., (ii) p-chloranil, $CH_2Cl_2$, r.t.

Step (a)

2,6-diMe PiperaIndoSiR (3.5 mg, 6.03 μmol) was dissolved in methanol (2 mL), and 3-fluorobenzaldehyde (1.3 μL, 12.06 μmol) and acetic acid (20 μL) were added, and stirred for 10 minutes at room temperature. Sodium cyanoborohydride (1.5 mg, 24 μmol) was added to the reaction solution, and stirred for 16 hours at room temperature. Water was added to the mixture, and the mixture was extracted by dichloromethane. The organic layer was dried by $Na_2SO_4$, and the solvent was distilled off under reduced pressure. Dichloromethane (5 mL) and p-chloranil (3 mg, 12.2 μmol) were added to the residue, and the solvent was distilled off under reduced pressure after stirring for three hours at room temperature. The residue was purified by HPLC (eluent, from 27% acetonitrile/0.1% trifluoroacetic acid/water (0 min) to 64% acetonitrile/0.1% TFA/water (20 min); flow rate=25.0 mL/min), and SiRpH3 (1.5 mg, 1.87 μmol, yield 31%) was obtained.

$^1$H NMR (400 MHz, $CD_3OD$): δ 0.60 (s, 6H, a), 1.97 (s, 6H, b), 3.01 (t, J=6.5 Hz, 2H, c), 3.38 (brs, 4H, d), 3.44 (s, 3H, e), 3.84 (brs, 4H, f), 4.03 (t, J=6.5 Hz, 2H, g), 4.38 (s, 2H, h), 6.82 (s, 1H, i), 6.90 (dd, J=9.4, 3.0 Hz, 1H, j), 6.99 (d, J=9.4 Hz, 1H, k), 7.23-7.38 (m, 6H, l), 7.45-7.56 (m, 3H, m); HRMS (ESI$^+$) Calcd for [M]$^+$, 574.3054, Found, 574.3032 (−2.2 mmu).

Example 3

(1) Synthesis of Compound 3

Compound 3 (SiRpH4) was synthesized by scheme 4 below.

Scheme 4

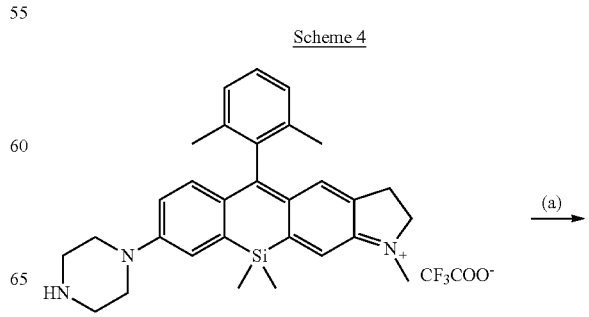

31

-continued

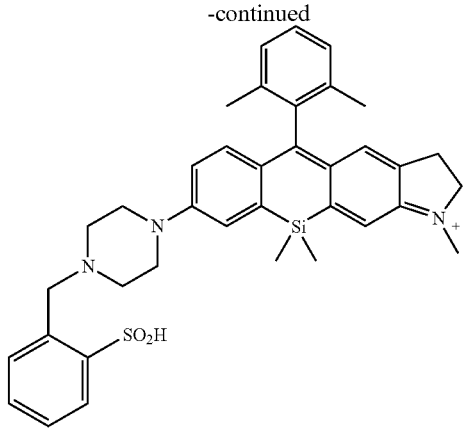

Compound 3

(a)(i) Benzaldehyde-2-sulfonic acid sodium salt, NaCNBH₃, AcOH, MeOH, r.t. (ii) p-chloranil, CH₂Cl₂, r.t.

2,6-diMe PiperaIndoSiR (2.4 mg, 4.16 µmol) was dissolved in methanol (2 mL), and sodium 2-formylbenzene-1-sulfonate (1.7 mg, 8.32 µmol) and acetic acid (2.4 µL, 41.6 µmol) were added, and stirred for 10 minutes at room temperature. Sodium cyanoborohydride (0.5 mg, 8.32 µmol) was added to the reaction solution, and stirred for 13 hours at room temperature. Water was added to the mixture, and the mixture was extracted by dichloromethane. The organic layer was dried by Na₂SO₄, and the solvent was distilled off under reduced pressure. Dichloromethane (2 mL) and p-chloranil (2 mg, 8.13 µmol) were added to the residue, and the solvent was distilled off under reduced pressure after stirring for three hours at room temperature. The residue was purified by HPLC (eluent, from 40% acetonitrile/0.1% trifluoroacetic acid/water (0 min) to 64% acetonitrile/0.1% TFA/water (20 min); flow rate=25.0 mL/min), and SiRpH4 (1.5 mg, 1.87 µmol, yield 31%) was obtained.

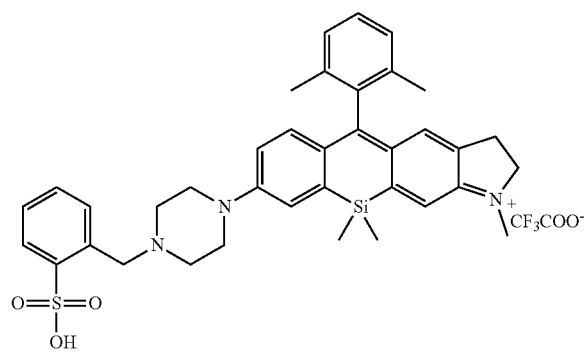

HRMS (ESI⁺) Calcd for [M]⁺, 636.2714, Found, 636.2675 (−3.9 mmu); The HPLC chromatogram after purification was as follows. The elution was done with a 20 min linear gradient from 48% CH₃CN/0.1% TFA az. To 80% CH₃CN/0.1% TFA aq. (flow rate=1.0 mL/min.); Absorbance at 600 nm was detected.

32

Example 4

(1) Synthesis of Compound 4

Compound 4 (SiRpH5) was synthesized by scheme 5 below.

Scheme 5

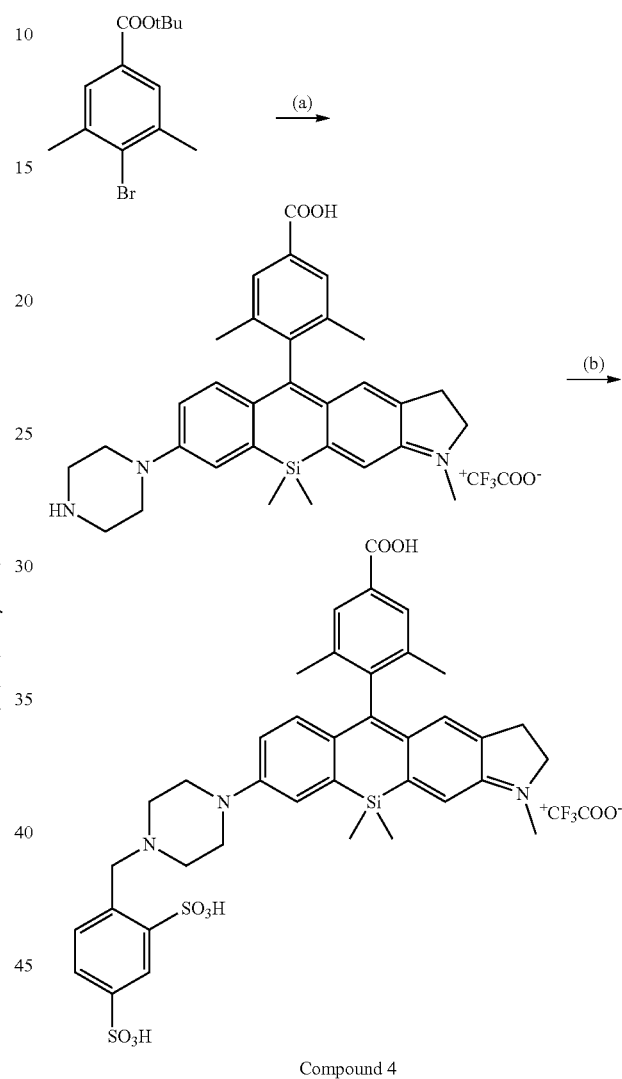

Compound 4

(a)(i) sec-BuLi, −78° C., (ii) BocPiperaIndoSiXanthone, THF, reflux, (iii) 2N HCl aq., r.t. (iv) TFA, r.t. (b)(i) Benzaldehyde-2,4-disulfonic acid disodium salt, 2.picoline borane, AcOH, MeOH.

(1) Step (a)

Dehydrated tetrahydrofuran (10 mL) was added to tert-butyl 4-bromo-3,5-dimethylbenzoate (182 mg, 0.638 mmol) in a dried, argon-purged flask, and the reaction solution was cooled to −78° C. 1 M sec-BuLi (0.64 mL, 0.64 mL [sic]) was added to the reaction solution, and stirred for 30 minutes at −78° C. BocPiperaIndoSiXanthone (61 mg, 0.128 mmol) was added to the reaction solution, and heated under reflux for 2.5 hours. After the reaction solution had returned to room temperature, the reaction was stopped by 2N hydrochloric acid aqueous solution, and the mixture was extracted by dichloromethane. The organic layer was dried by Na$_2$SO$_4$, and the solvent was distilled off under reduced pressure. Trifluoroacetic acid (5 mL) was added to the residue, and stirred for 30 minutes at room temperature. After washing with hexane, the residue was purified by HPLC (eluent, from 24% acetonitrile/0.1% trifluoroacetic acid/water (0 min) to 64% acetonitrile/0.1% TFA/water (20 min); flow rate=25.0 mL/min), and 4-COOH-2,6-diMe PiperaIndoSiR (50 mg, 80.2 µmol, yield 63%) was obtained.

$^1$H NMR (300 MHz, CD$_3$CN): δ 0.56 (s, 6H, a), 2.00 (s, 6H, b), 2.91 (t, J=6.1 Hz, 2H, c), 3.30 (t, J=4.5 Hz, 4H, d), 3.33 (s, 3H, e), 3.81 (t, J=4.5 Hz, 4H, f), 3.94 (t, J=6.1 Hz, 4H, g), 6.73-6.77 (m, 2H, h), 6.87 (d, J=9.6 Hz, 1H, i), 7.29 (s, 1H, j), 7.36 (d, J=2.4 Hz, 1H, k), 7.86 (s, 2H, 1); $^{13}$C NMR (100 MHz, CD$_3$OD) δ −1.39, 19.84, 26.39, 35.08, 43.68, 44.41, 56.88, 116.00, 119.30, 121.79, 129.64, 129.99, 132.04, 133.46, 137.28, 137.43, 137.60, 144.22, 144.64, 152.62, 156.24, 160.24, 164.39, 168.28; HRMS (ESI$^+$) Calcd for [M]$^+$, 510.2577, Found, 510.2557 (−2.0 mmu).

(2) Step (b)

4-COOH-2,6-diMe PiperaIndoSiR (12.8 mg, 20.5 µmol) was dissolved in methanol (5 mL), and disodium 4-formylbenzene-1,3-disulfonate (19.1 mg, 61.5 µmol) and acetic acid (250 µL) were added, and stirred for 30 minutes at room temperature. 2-Picoline borane (4.4 mg, 41 µmol) was added to the reaction solution, and stirred for 16 hours at room temperature. The solvent of the mixture was distilled off under reduced pressure. The residue was purified by HPLC (eluent, from 28% acetonitrile/0.1% trifluoroacetic acid/water (0 min) to 60% acetonitrile/0.1% TFA/water (20 min); flow rate=25.0 mL/min), and SiRpH5 (11.2 mg, 12.8 µmol, yield 63%) was obtained.

$^1$H NMR (400 MHz, 20 mM pD 9.7 phosphate buffered D$_2$O): δ 0.48 (s, 6H, a), 1.87 (s, 6H, b), 2.63 (brs, 4H, c), 2.81 (t, J=7.0 Hz, 2H, d), 3.31 (s, 3H, e), 3.50 (brs, 4H, f), 3.90 (t, J=7.0 Hz, 4H, g), 4.00 (s, 2H, h), 6.51 (d, J=9.4 Hz, 1H, i), 6.75 (s, 1H, j), 6.84 (d, J=9.4 Hz, 1H, k), 7.28 (s, 1H, l), 7.38 (s, 1H, m), 7.65 (s, 2H, n), 7.72 (d, J=8.2 Hz, 1H, o), 7.88 (d, J=8.2 Hz, 1H, p), 8.30 (s, 1H, q); $^{13}$C NMR (100 MHz, CD$_3$OD:D$_2$O=1:3) δ −1.11, 20.10, 26.73, 35.45, 45.53, 52.91, 57.57, 59.77, 117.07, 119.58, 120.19, 122.40, 126.87, 129.41, 130.21, 130.34, 130.81, 131.79, 133.57, 135.96, 137.56, 138.12, 138.47, 144.92, 145.32, 146.11, 147.92, 152.72, 157.61, 160.90, 163.91, 170.85; HRMS (ESI$^+$) Calcd for [M]$^+$, 760.2183, Found, 760.2137 (−4.6 mmu).

Example 5

The spectral characteristics of compound 1 of the present invention (2,6-diMe BnPiperaIndoSiR) were evaluated. The absorption spectrum, fluorescence spectrum, and excitation spectrum were measured using a Shimadzu UV-1650PC absorption spectrophotometer and a Hitachi F-4500 fluorometer. The results are shown in FIGS. 2a-e.

Figure 2A:
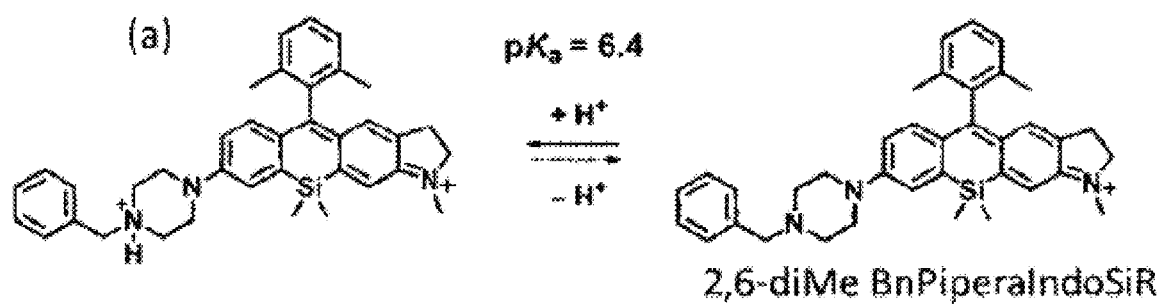
FIG. 2a is the assumed chemical equilibrium equation of 2,6-diMe BnPiperaIndoSiR.
Figure 2B:
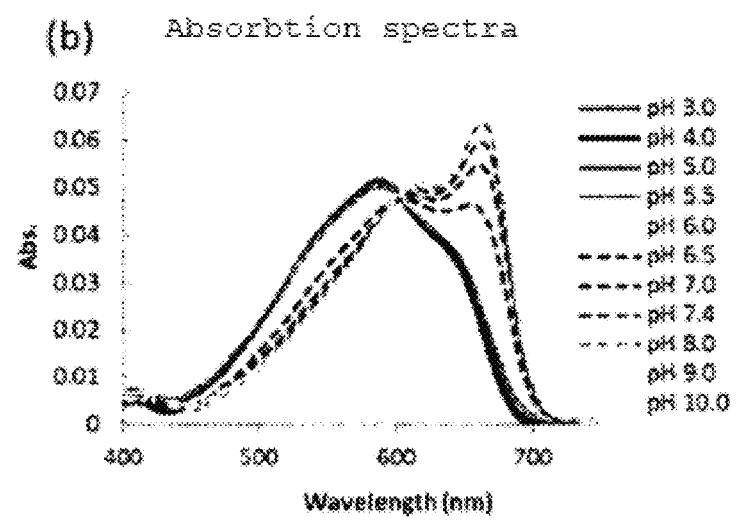
FIG. 2b is the absorption spectra of 2,6-diMe BnPiperaIndoSiR in 100 mM sodium phosphate buffer (including 1% DMSO) of different pH.
Figure 2C:
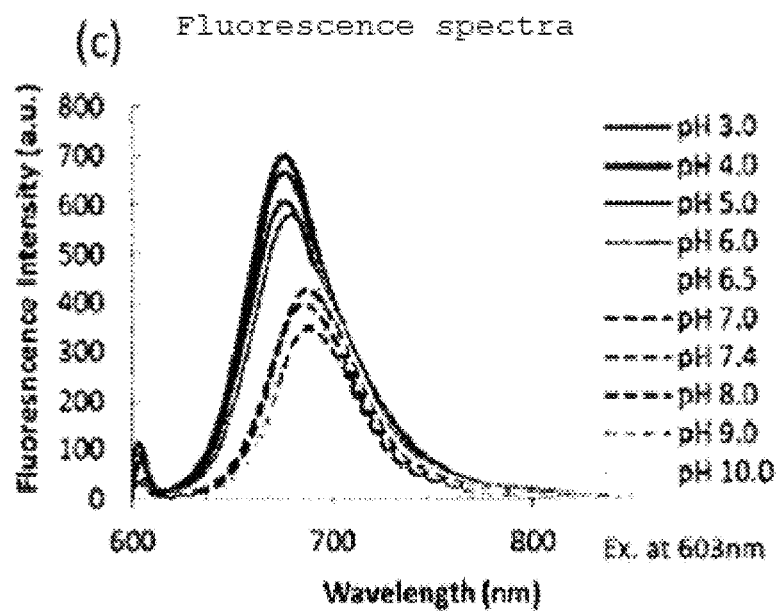
FIG. 2c is the fluorescence spectra of 2,6-diMe BnPiperaIndoSiR in 100 mM sodium phosphate buffer (including 1% DMSO) of different pH.
Figure 2D:
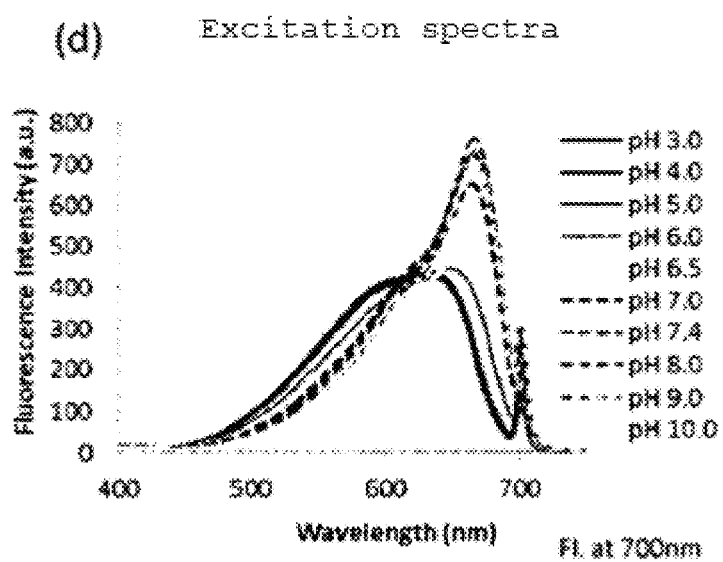
FIG. 2d is the excitation spectra of 2,6-diMe BnPiperaIndoSiR in 100 mM sodium phosphate buffer (including 1% DMSO) of different pH.
Figure 2E:
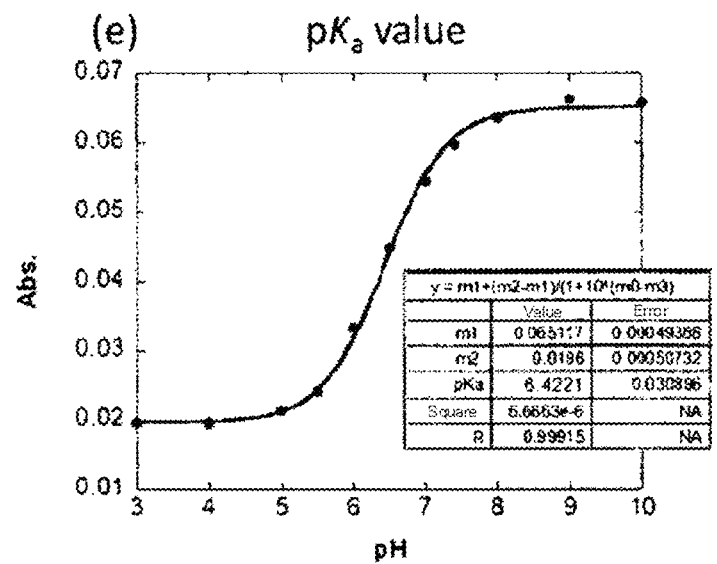
FIG. 2e is a plot of the changes in absorbance at 663 nm when the pH changed.

FIG. 2a represents the assumed chemical equilibrium equation of 2,6-diMe BnPiperaIndoSiR. FIGS. 2b, 2c, and 2d respectively represent the absorption, fluorescence, and excitation spectra of 2,6-diMe BnPiperaIndoSiR in 100 mM sodium phosphate buffer (containing 1% DMSO) of different pH. FIG. 2e calculated the pK$_a$=6.4 of the protonation reaction by plotting the changes in absorbance at 663 nm when the pH was varied.

Looking at the excitation spectra, 2,6-diMe BnPiperaIndoSiR is understood to function as a ratio type pH probe since the 580 nm absorbance decreases and the 663 nm absorbance rises as the pH of the solvent moves from acidic to basic. Its pK$_a$ also decreased 0.9 in comparison to 2-Me MePiperaIndoSiR (compound with an N-methylpiperazine ring introduced) by benzylation of the piperazine aliphatic amino group. This is thought to be due to the electron withdrawing effect of the benzyl group.

Table 1 shows the optical characteristics of 2,6-diMe BnPiperaIndoSiR measured in 100 mM sodium phosphate buffer. The pK$_a$ value of 2,6-diMe BnPiperaIndoSiR showed a relatively high quantum fluorescence yield on both the acidic side and basic side.

TABLE 1

| | Abs$_{max}$ [nm] | Em$_{max}$ [nm] | Φ$_{fl}$ | E(M$^{-1}$ cm$^{-1}$) |
|---|---|---|---|---|
| 2,6-diMe BnPiperaIndoSiR (pH 3.0) | 588 | 676 | 0.19 | 26,000 |
| 2,6-diMe BnPiperaIndoSiR (pH 10.0) | 663 | 689 | 0.12 | 33,000 |

Example 6

The spectral characteristics of compound 2 of the present invention (SiRpH3) were evaluated. The absorption spectrum fluorescence spectrum, and excitation spectrum were measured using a Shimadzu UV-1650PC absorption spectrophotometer and a Hitachi F-4500 fluorometer. The results are shown in FIGS. 3a-c.

Figure 3A:
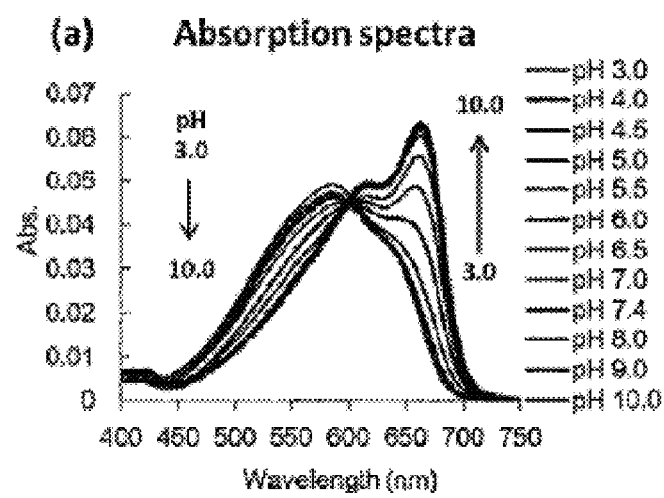
FIG. 3a is the absorption spectra of; SiRpH3 in 100 mM sodium phosphate buffer (including 1% DMSO) of different pH.
Figure 3B:
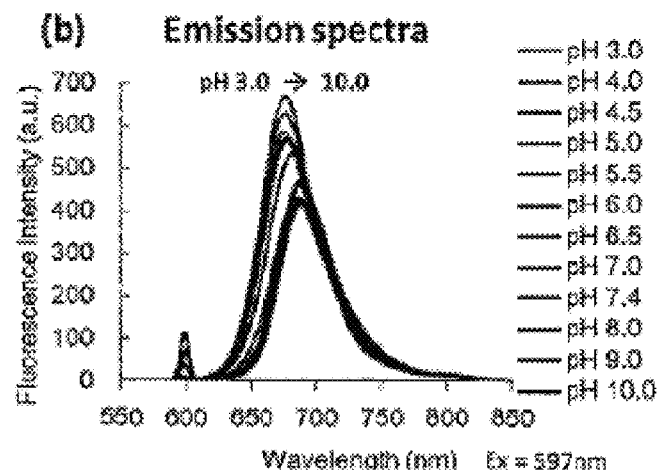
FIG. 3b is the fluorescence spectra of; SiRpH3 in 100 mM sodium phosphate buffer (including 1% DMSO) of different pH.
Figure 3C:
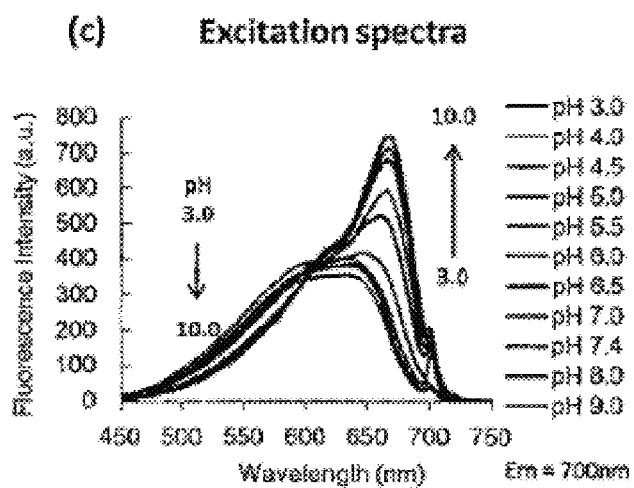
FIG. 3c is the excitation spectra of; SiRpH3 in 100 mM sodium phosphate buffer (including 1% DMSO) of different pH.
Figure 3D:
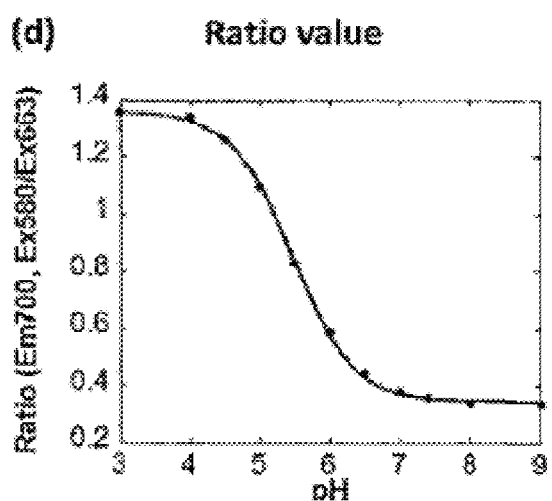
FIG. 3d is a plot relative to pH of the fluorescence intensity ratio (ratio) of SiRpH3 when the 700 nm fluorescence intensity when excited at 580 nm was divided by the fluorescence intensity when excited at 663 nm.

FIGS. 3a, 3b, and 3c represent the absorption, fluorescence, and excitation spectra of SiRpH3 in 100 mM sodium phosphate buffer (containing 1% DMSO) of different pH. FIG. 3d shows a plot relative to pH of the fluorescence intensity ratio (ratio) when the 700 nm fluorescence intensity when excited at 580 nm was divided by the fluorescence intensity when excited at 663 nm.

The absorption wavelength of compound 2 of the present invention lengthened greatly, approximately 80 nm, from approximately 580 nm to approximately 660 nm, as the pH of the solution moved from acidic to basic. On the other hand, the fluorescence wavelength did not change greatly even when the pH of the solution changed. Based on this characteristic, it was possible to calculate the pH of a solution in a cuvette by measuring the ratio in the cuvette.

Table 2 shows the optical characteristics of SiRpH3 measured in 100 mM sodium phosphate buffer.

SiRpH3 in which the fluorine atom has been substituted has absorption maxima at approximately 580 nm and approximately 660 nm in accordance with the pH, in the same way as 2,6-diMe BnPiperaIndoSiR, and shows adequate fluorescence quantum yield as a fluorescent probe.

TABLE 2

| | Abs$_{max}$ [nm] | Em$_{max}$ [nm] | E(M$^{-1}$cm$^{-1}$) | Φ$_{fl}$ |
|---|---|---|---|---|
| pH 3.0 | 585 | 676 | 25,000 | 0.20 |
| pH 7.4 | 662 | 688 | 30,000 | 0.12 |
| pH 10.0 | 663 | 689 | 31,000 | 0.11 |

Example 7

The spectral characteristics of compound 3 of the present invention (SiRpH4) were evaluated. The absorption spectrum fluorescence spectrum, and excitation spectrum were measured using a Shimadzu UV-1650PC absorption spectrophotometer and a Hitachi F-4500 fluorometer. The absorption spectra and excitation spectra are shown in FIGS. 4a and 4b.

Figure 4A:
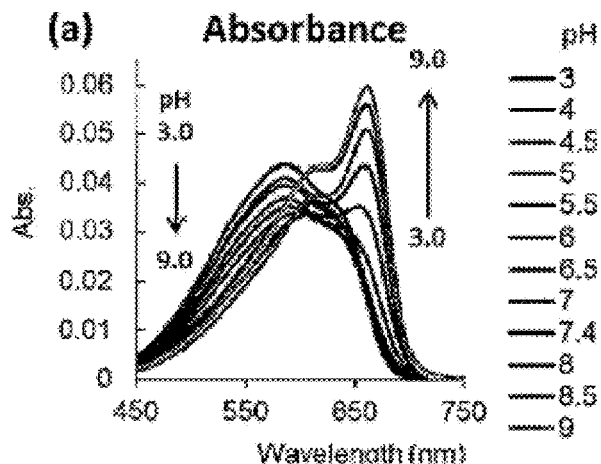
FIG. 4a is the absorption spectra of; SiRpH4 in 100 mM sodium phosphate buffer (including 1% DMSO) of different pH.
Figure 4B:
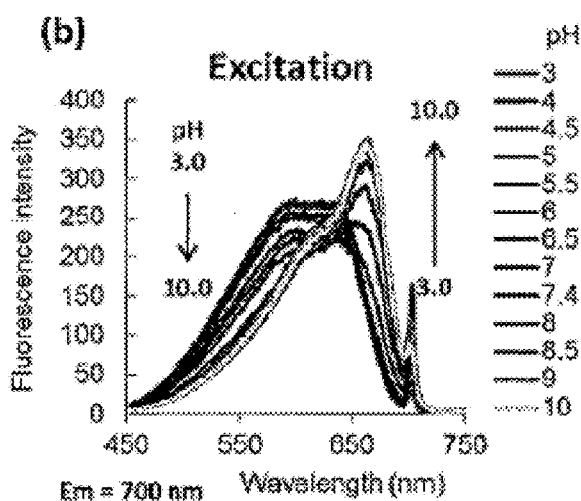
FIG. 4b is the excitation spectra of; SiRpH4 in 100 mM sodium phosphate buffer (including 1% DMSO) of different pH.
Figure 4C:
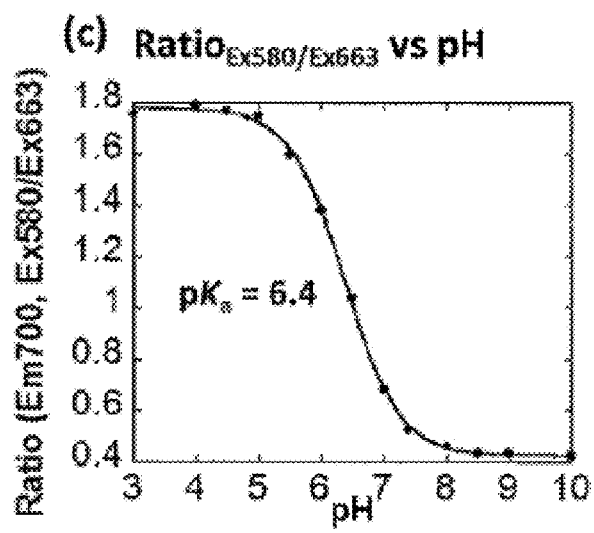
FIG. 4c is a plot relative to pH of the fluorescence intensity ratio (ratio) of SiRpH4 when the 700 nm fluorescence intensity when excited at 580 nm was divided by the fluorescence intensity when excited at 663 nm.

FIGS. 4a and 4b represent the absorption and excitation spectra of SiRpH4 in 100 mM sodium phosphate buffer (containing 1% DMSO) of different pH. FIG. 4c shows a plot relative to pH of the fluorescence intensity ratio (ratio) when the 700 nm fluorescence intensity when excited at 580 nm was divided by the fluorescence intensity when excited at 663 nm.

SiRpH4 presented the same optical characteristics as SiRpH3, but the pKa of the ratio value change shifted to the basic side in comparison to SiRpH3 due to the ortho position sulfone group.

Example 8

The spectral characteristics of compound 4 of the present invention (SiRpH5) were evaluated. The absorption spectrum fluorescence spectrum, and excitation spectrum were measured using a Shimadzu UV-1650PC absorption spectrophotometer and a Hitachi F-4500 fluorometer. The absorption spectra and excitation spectra are shown in FIGS. 5b and 5c.

Figure 5A:
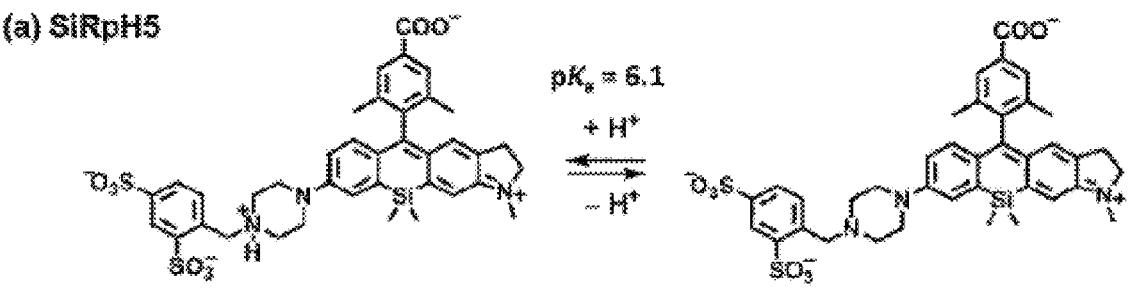
FIG. 5a is the assumed chemical equilibrium equation of SiRpH5.
Figure 5B:
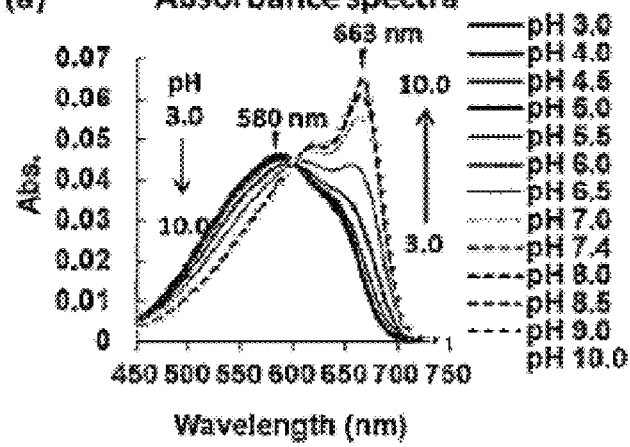
FIG. 5b is the absorption spectra of; SiRpH5 in 100 mM sodium phosphate buffer (including 1% DMSO) of different pH.
Figure 5C:
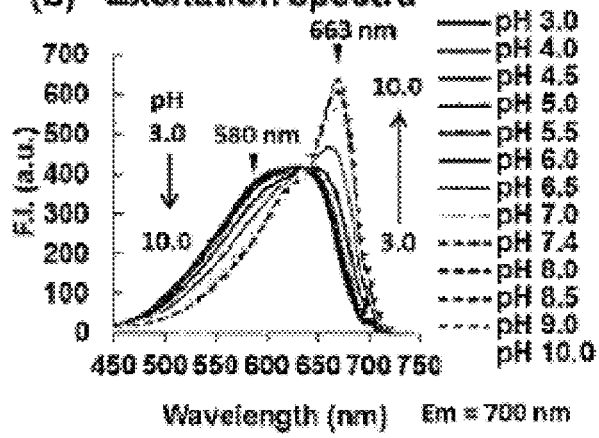
FIG. 5c is the excitation spectra of; SiRpH5 in 100 mM sodium phosphate buffer (including 1% DMSO) of different pH.
Figure 5D:
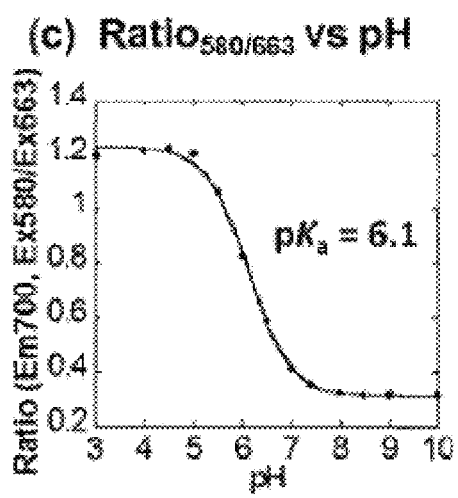
FIG. 5d is a plot relative to pH of the fluorescence intensity ratio (ratio) of SiRpH5 when the 700 nm fluorescence intensity when excited at 580 nm was divided by the fluorescence intensity when excited at 663 nm.

FIG. 5a represents the assumed chemical equilibrium equation of SiRpH5. FIGS. 5b and 5c represent the absorption and excitation spectra of SiRpH5 in 100 mM sodium phosphate buffer (containing 1%) DMSO) of different pH. FIG. 5d shows a plot relative to pH of the fluorescence intensity ratio (ratio) when the 700 nm fluorescence intensity when excited at 580 nm was divided by the fluorescence intensity when excited at 663 nm. The $pK_a$=6.1 of the protonation reaction was calculated from this plot.

SiRpH5 presented the same optical characteristics as SiRpH4, but the pKa of the ratio value change shifted to the acidic side in comparison to SiRpH4 due to the para position sulfone group, showing a value suited to the measurement of acidic organelles.

Table 3 shows the optical characteristics of SiRpH5 measured in 100 mM sodium phosphate buffer.

SiRpH5 has absorption maxima at approximately 590 nm and approximately 670 nm, and presented adequate fluorescence quantum yield as a fluorescent probe.

TABLE 3

|  | $\lambda_{ex}$ (nm) | $\lambda_{em}$ (nm) | $\varepsilon$ (M$^{-1}$cm$^{-1}$) | $\Phi_{fl}$ |
| --- | --- | --- | --- | --- |
| pH 3.0 | 588 | 679 | 23,000 | 0.21 |
| pH 10.0 | 668 | 690 | 33,000 | 0.08 |

Figure 6:
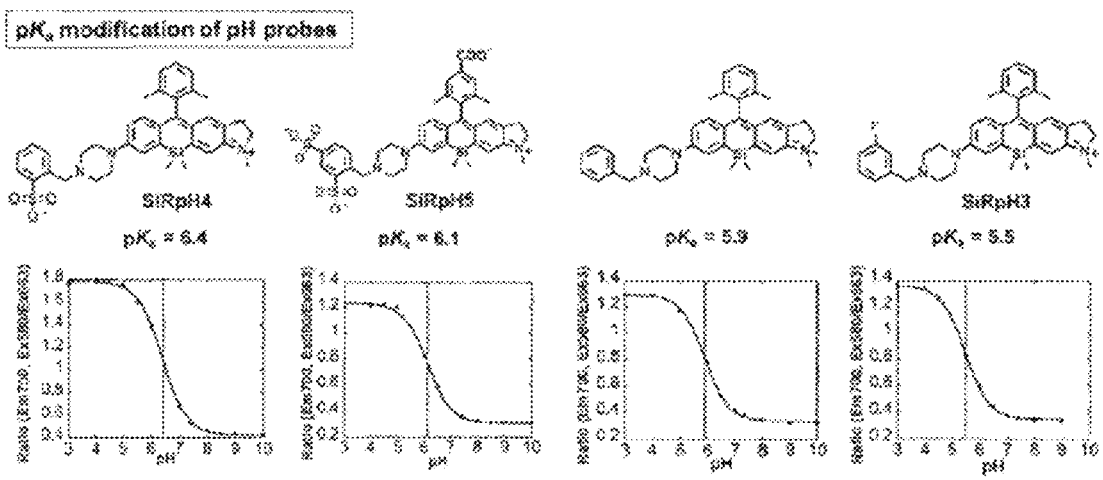
FIG. 6 is a plot of the ratio value of various compounds vs. pH.

FIG. 6 shows a ratio value of each compound vs. pH plot. As above, the drawing showed that the $pK_a$ of a pH probe can be adjusted freely by introducing various substituents onto the benzyl group. Since the organelles in a cell each have a unique pH, the pH of each organelle can be measured more accurately by developing and using pH probes having a $pK_a$ suited to pH measurement of each organelle by utilizing this pH probe mother nucleus.

Synthesis of SiRpH5 with a biopolymer label site introduced

Example 9

SiRpH5-PEG$_6$-SE (compound 6) having an N-hydroxysuccinylimidiyl [sic] ester via a PEG linker and capable of forming a covalent bond with an amino group of a biopolymer was synthesized by scheme 6 below.

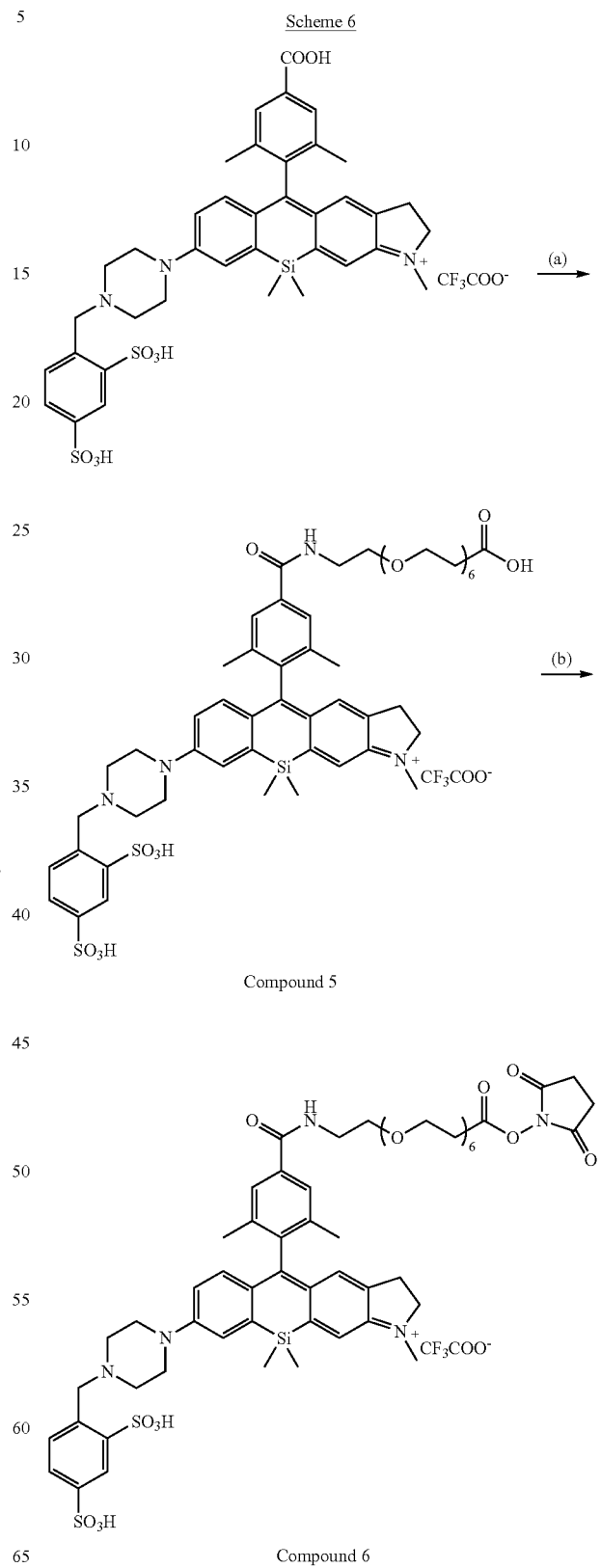

Scheme 6

(a)(i) EDC.HCl, DIPEA, NHS, DMF, r.t., (ii) NH$_2$-PEG$_6$-OH, DIPEA, DMF, r.t., (b) EDC.HCl, DIPEA, NHS, DMF, r.t.

Steps (a) and (b)

SiRpH5 (15 mg, 17.2 μmol), N-hydroxysuccinimide (2.2 mg, 18.9 μmol), EDC hydrochloride (3.6 mg, 18.9 mmol), and DMF (2 mL) were added to a flask; DIPEA (6.6 μL, 37.8 μmol) was then added, and stirred for 20 hours at room temperature. The reaction solution was purified by HPLC (eluent, from 28% acetonitrile/0.1% trifluoroacetic acid/water (0 min) to 60% acetonitrile/0.1% TFA/water (20 min); flow rate=25.0 mL/min), and the solvent was distilled off under reduced pressure. NH$_2$-PEG$_6$-OH (4.9 mg, 13.7 μmol), DIPEA (25 μL, 0.14 mmol), and water (50 μL) were added to the residue, and stirred for 15 hours at room temperature. The reaction solution was purified by HPLC (eluent, from 28% acetonitrile/0.1% trifluoroacetic acid/water (0 min) to 60% acetonitrile/0.1% TFA/water (20 min); flow rate=25.0 mL/min), and the solvent was distilled off under reduced pressure (SiRpH5-PEG$_6$-OH). N-hydroxysuccinimide (4 mg, 35 μmol), EDC hydrochloride (6.7 mg, 0.11 mmol), and DMF (3 mL) were added to the residue; DIPEA (20 μL, 37.8 μmol) was then added, and stirred for 17 hours at room temperature. The reaction solution was purified by HPLC (eluent, from 24% acetonitrile/0.1% trifluoroacetic acid/water (0 min) to 44% acetonitrile/0.1% TFA/water (20 min); flow rate=25.0 mL/min), and SiRpH5-PEG$_6$-SE (4.1 mg, 3.44 μmol, yield 27%) was obtained.

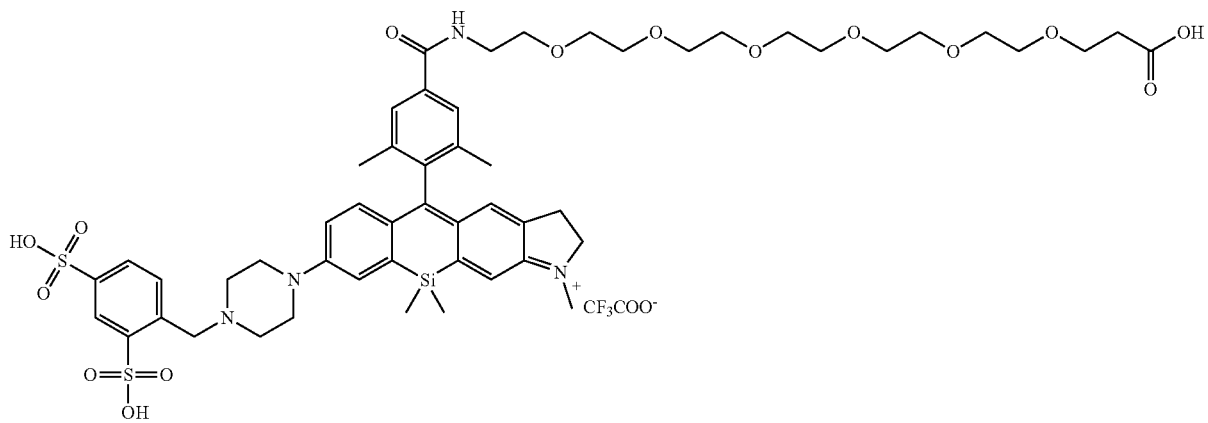

$^1$H BNR (400 MHz, D$_2$O:CH$_3$CN=3:1): δ 0.61 (s, 6H), 2.05 (s, 6H), 2.60 (t, J=6.2 Hz 2H), 2.98 (t, J=6.2 Hz, 2H), 3.34 (brs, 4H), 3.42 (s, 3H), 3.61-3.76 (m, 30H), 4.05 (t, J=6.2 Hz, 2H), 4.77 (s, 2H), 6.80 (s, 1H), 6.87 (dd, J=9.0, 2.4 Hz, 1H), 6.95 (d, J=9.0 Hz, 1H), 7.41 (s, 1H), 7.46 (d, J=2.4 Hz, 1H), 7.71-7.73 (m, 3H), 8.02 (dd, (J=8.0, 1.8 Hz, 1H), 8.34 (d, J=1.8 Hz, 1H); HRMS (ESI$^+$) Calcd for [M]$^+$, 1095.4127, Found, 1095.4156 (+2.9 mmu); The HPLC chromatogram after purification was as follows. The elution was done with a 20 min linear gradient from 16% CH$_3$CN/0.1% TFA aq. To 48% CH$_3$CN/0.1% TFA aq. (flow rate=1.0 mL/min); Absorbance at 600 nm was detected.

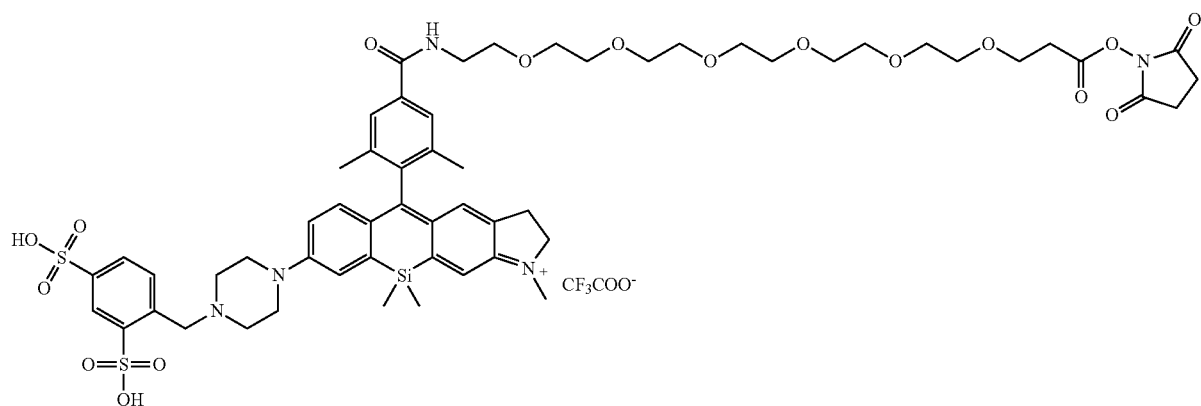

HRMS (ESI⁺) Calcd for [M]⁺, 1192.4290, Found 1192.4270 (−2.0 mmu)

Example 10

SiRpH5-PEG₆-BG (compound 7) having a benzylguanine structure via a PEG linker and capable of forming a covalent bond with a SNAP-Tag protein was synthesized by scheme 7 below.

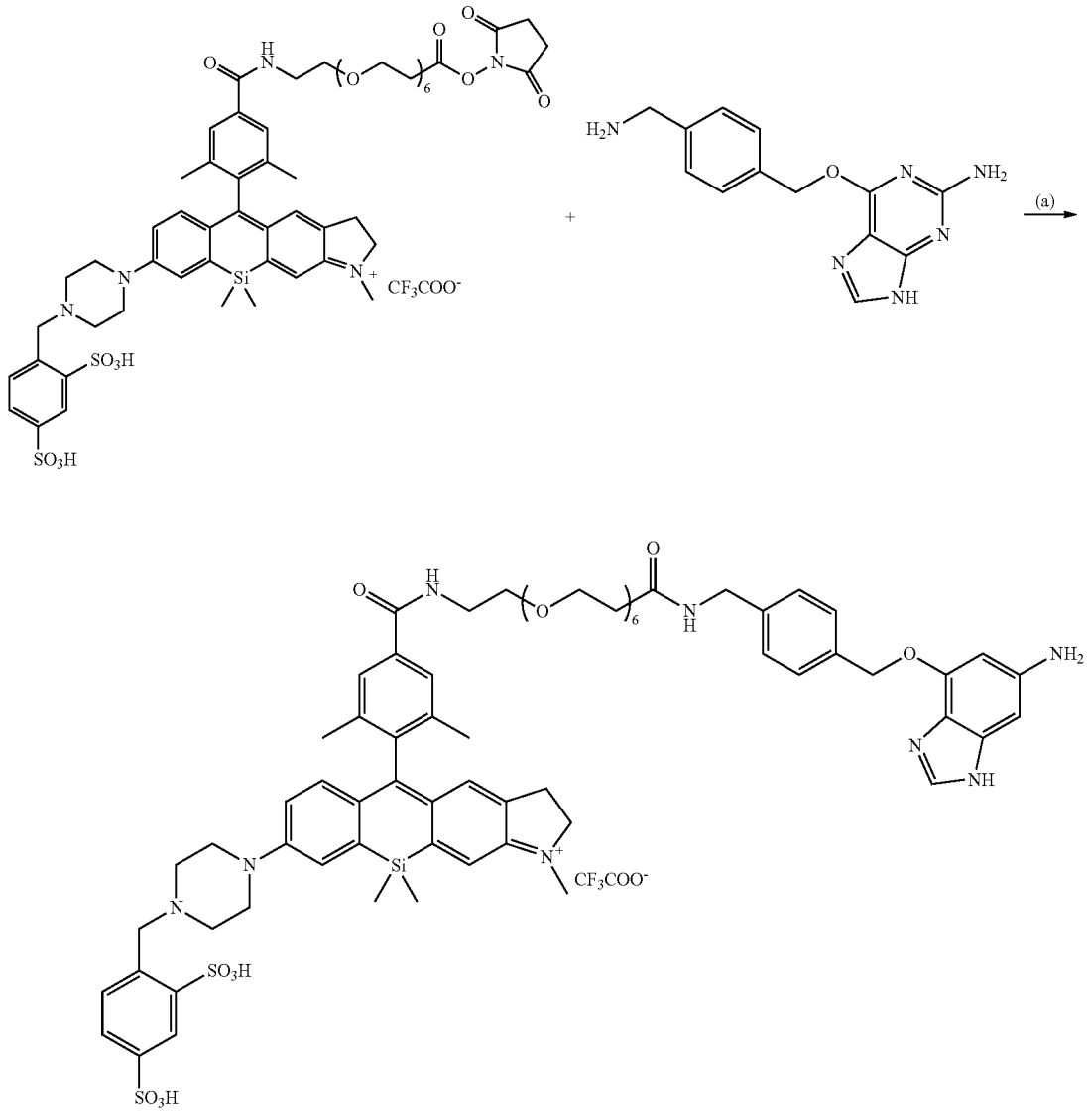

Compound 7

(a) DIPEA, DMF, r.t.

Step (a)

SiRpH5-PEG₆-SE (1.8 mg, 1.38 μmol), BG-NH₂ (1.1 mg, 4.14 μmol), and DMF (1 mL) were added to a flask; DIPEA (1.4 μL, 8.28 μmol) was then added, and stirred for four hours at room temperature. The reaction solution was purified by HPLC (eluent, from 16% acetonitrile/0.1% trifluoroacetic acid/water (0 min) to 48% acetonitrile/0.1% TFA/water (20 min); flow rate=25.0 mL/min), and SiRpH5-PEG₆-BG (1.7 mg, 1.16 μmol, yield 84%) was obtained.

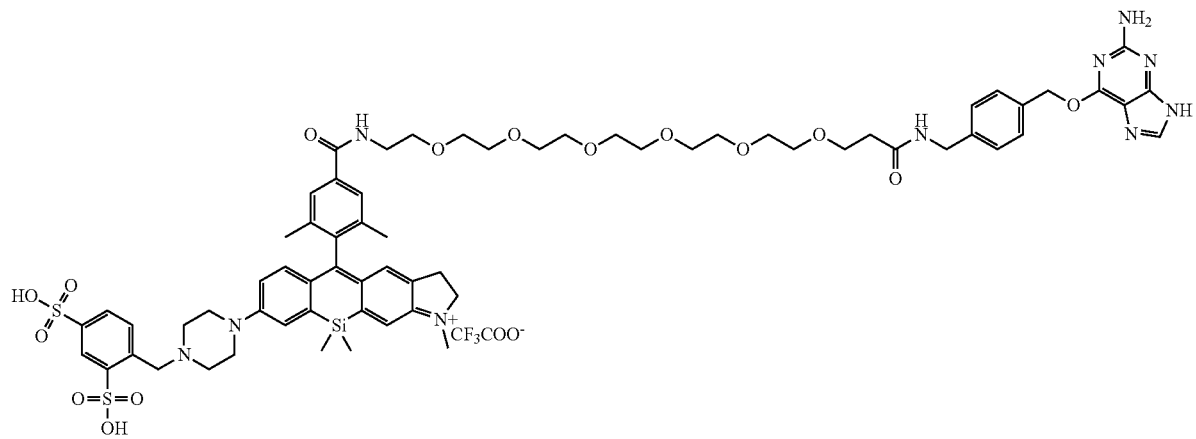

HRMS (ESI⁺) Calcd for [M]⁺, 1347.4204, Found, 1347.5250 (−4.6 mmu); The HPLC chromatogram after purification was as follow. The elution was done with a 20 min linear gradient from 24% $CH_3CN$/0.1% TFA aq. To 56% $CH_3CN$/0.1% TFA aq. (flow rate=1.0 mL/min.); Absorbance at 600 nm was detected.

Example 11 pH Measurement of Intracellular Organelles Using SiRpH5

(A) pH Measurement of Lysosomes

It is known that dextran, a polysaccharide, is accumulated selectively in lysosomes by adding dextran to the extracellular fluid and incubating for several hours after it has been taken up into the cells. SiRpH5-Dex, which is SiRpH5 labeled by 10 kDa aminodextran, was prepared for conducting pH measurement of lysosomes using this probe.

(1) Preparation Method 10 kDa aminodextran (1.3 mg, 0.13 μmol) and 0.1 M sodium bicarbonate aqueous solution (460 μL) were added to a reactor. A solution of SiRpH5-PEG₆-SE (0.64 μg, 0.49 μmol) dissolved in 160 μL of DMSO was then added, and stirred for four hours at room temperature. The reaction solution was purified using a PD-10 gel filtration column (GE Healthcare) and freeze dried to obtain SiRpH5-Dex. A 10 mg/mL SiRpH5-Dex aqueous solution was prepared, and the average labeling rate of the probe was determined to be 2.6 nmol probe/1 nmol dextran by measurement of absorbance.

Figure 7A:
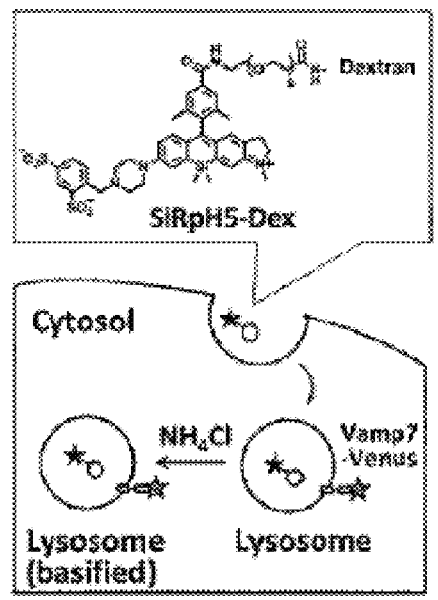
FIG. 7a is an image diagram of a study of pH measurement of a lysosome using SiRpH5-Dex.

(2) pH Measurement of Lysosomes (a) Study image (see FIG. 7a): SiRpH5-Dex was accumulated in the lysosomes, and the pH of the lysosomes was then made basic by adding ammonium chloride aqueous solution, which is a lysosomal basic reagent.

Figure 7B:
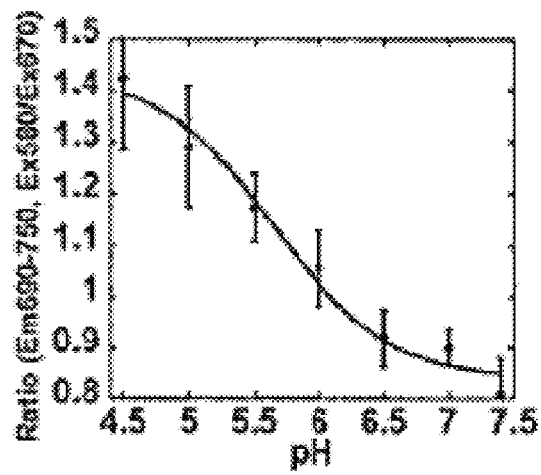
FIG. 7b is a calibration curve of intracellular pH produced using SiRpH5-Dex.

(b) FIG. 7b shows the intracellular pH calibration curve prepared when the SiRpH5-Dex-loaded cells were fixed by 10% formalin, the extracellular fluid was replaced by pH 4.5-7.4 sodium phosphate buffer, and imaging was conducted.

Figure 7C:
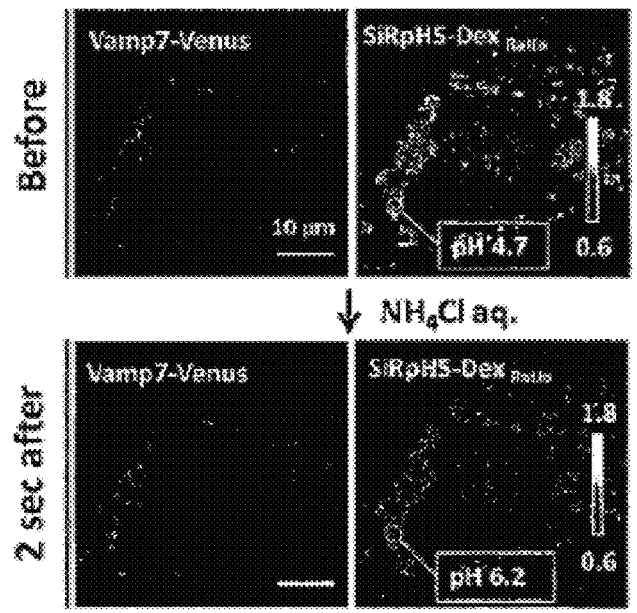
FIG. 7c is the results of pH measurement of a lysosome when observed by confocal microscope.

(c) MEF cells were incubated for two hours in medium including 200 μg/mL of SiRpH5-Dex. The medium was then replaced by probe-free medium, and the cells were incubated for three hours. When examined by confocal microscope, fluorescence derived from SiRpH5-Dex was observed from the vicinity of a fusion protein of Vamp7, which is a lysosomal marker protein, and the yellow fluorescent protein Venus (FIG. 7c). The pH calculated using the calibration curve from the ratio value of the site surrounded by the dotted line was 4.7. When the final concentration 33 mM ammonium chloride aqueous solution was added thereafter, the pH of the lysosomes was understood to become basic up to 6.2. It was understood that the pH can be measured within live cells using the present invention because these values are comparable to the reported pH of lysosomes and the pH of lysosomes after basifying reagent addition.

(B) Measurement of pH of Recycling Endosomes

Transferrin (Tfn), an iron transport protein, is known to be endocytosed via transferrin receptors (TfnR), transported into early endosomes, and then transported into recycling endosomes. SiRpH5-Tfn, which is SiRpH5 labeled by holotransferrin, an iron ion-transferring complex, was prepared to measure the pH of recycling endosomes using the probe.

(1) Preparation Method

Holotransferrin (9.04 mg, 0.113 μmol) and 1000 μL of 0.1 M borate buffer (pH 8.0) were added to a reactor. A solution obtained by dissolving SiRpH5-PEG₆-SE (1.18 mg, 0.91 μmol) in 200 μL of DMSO and 800 μL of 0.1 M borate buffer (pH 8.0) was then added to the reactor, and stirred for one hour at room temperature. The reaction solution was purified using a PD-10 gel filtration column (GE Healthcare) and freeze dried to obtain SiRpH5-Tfn. A 5 mg/mL SiRpH5-Tfn aqueous solution was prepared, and the average labeling rate of the probe was determined to be 7.3 nmol probe/1 nmol Tfn by measurement of absorbance.

Figure 8A:
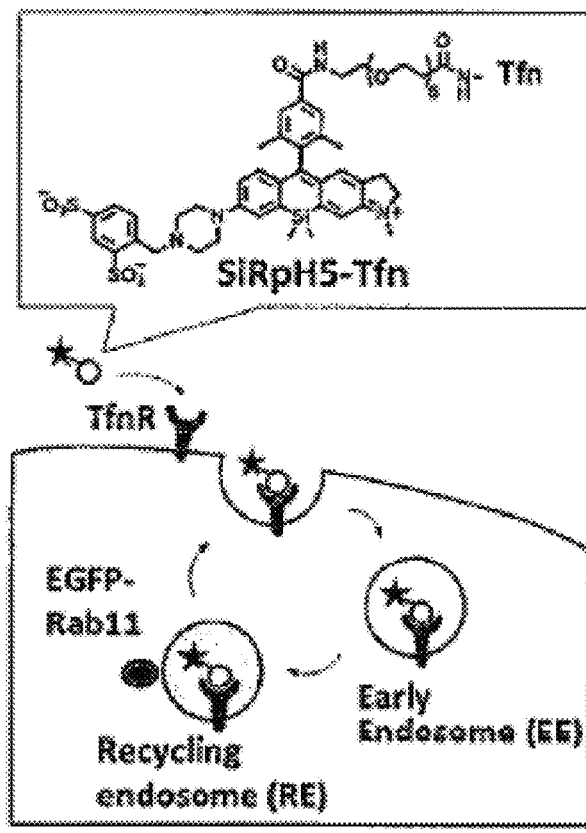
FIG. 8a is an image diagram of a study of measurement of the pH of a recycling endosome using SiRpH5-Tfn.

(2) pH Measurement of Recycling Endosomes (a) Study image (see FIG. 8a): SiRpH5-Tfn was accumulated in recycling endosomes (RE), and the pH was measured.

Figure 8B:
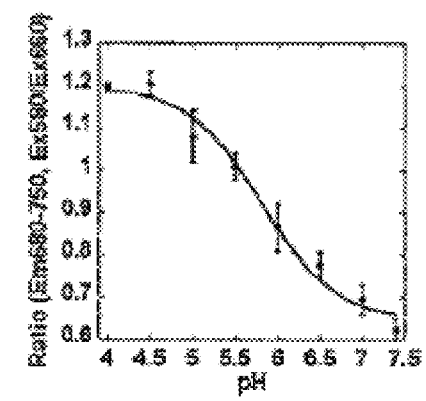
FIG. 8b is a calibration curve of intracellular pH produced using SiRpH5-Tfn.

(b) FIG. 8b shows the intracellular pH calibration curve when the SiRpH5-Tfn-loaded cells were fixed by 4% formaldehyde, the extracellular fluid was replaced by pH 4.0-7.4 HEPS buffer, and imaging was conducted.

Figure 8C:
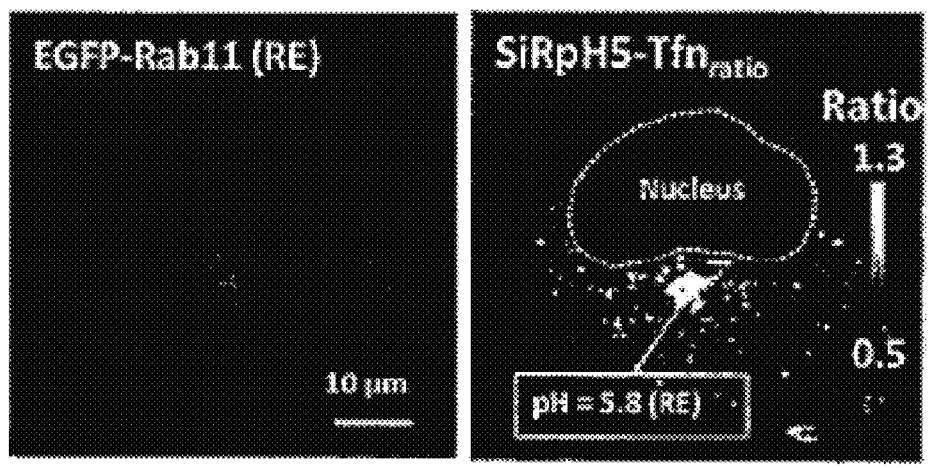
FIG. 8c is the results of pH measurement of a recycling endosome when observed by confocal microscope.
Figure 9A:
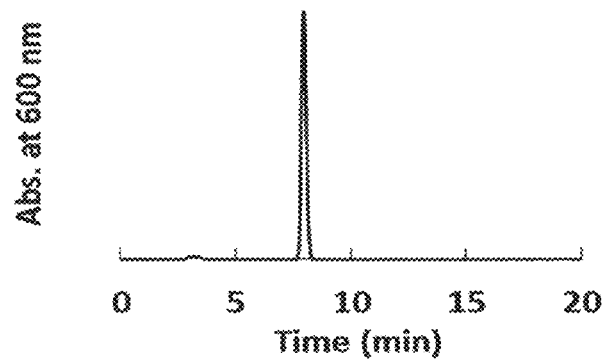
FIG. 9a is the result of the HPLC chromatogram after purification of Compound 3.
Figure 9B:
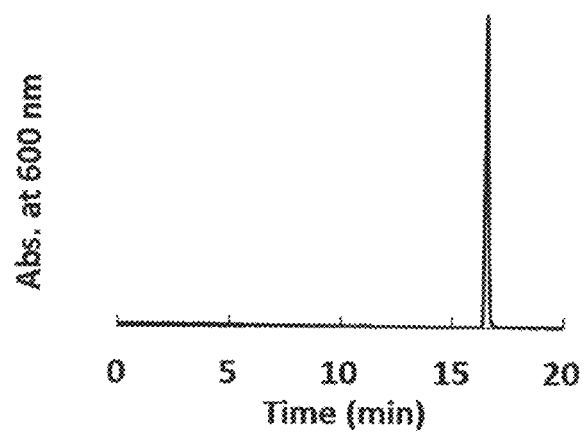
FIG. 9b is the result of the HPLC chromatogram after purification of Compound 5.
Figure 9C:
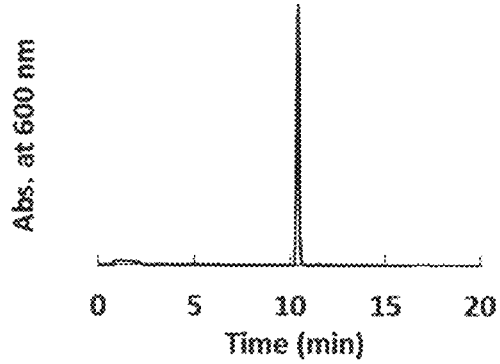
FIG. 9c is the result of the HPLC chromatogram after purification of Compound 7.

(c) COS-1 cells were incubated for 50 minutes in buffer including 25 μg/mL of SiRpH5-Tfn. The buffer was then replaced by probe-free buffer, and the cells were incubated for 15 minutes. Images were taken by confocal microscope (FIG. 8c). Fluorescence derived from SiRpH5-Tfn was observed from a site that overlapped with a fusion protein of Rab11, which is a recycling endosome marker protein, and the green fluorescent protein GFP. The pH calculated using the calibration curve from the ratio value of the recycling endosomes surrounded by the dotted line was 5.8. This value was comparable to the reported value of recycling endosomes.

It appears on this basis that the pH of various intracellular organelles can be measured by varying the protein used to label the probe.

As shown in the examples, it was understood that the $pK_a$ of the pH probe can be adjusted easily by introducing an electron withdrawing substituent on the piperazine ring amino group. Further adjustment of the $pK_a$, such as raising or lowering it, is believed to be possible, for example, by introducing electron withdrawing groups and electron donating groups on the benzene ring of the benzyl group.

The fluorophore Si rhodamine used as the mother nucleus of the pH probes in the examples is a fluorescent dye having a high fluorescence quantum yield and resistance to photobleaching. The present invention therefore can achieve highly accurate imaging of target molecules labeled by a small amount of molecule, which was difficult with conventional pH probes of low fluorescence quantum yield, and time lapse imaging requiring prolonged excitation light irradiation. In addition, since the environmental sensitivity is low, highly reliable pH measurement is expected to be possible in various organelles within cells. Furthermore, since the $pK_a$ of the pH probe can be adjusted arbitrarily, pH probes suitable for visualizing various pH regions from acidic to basic can be developed by matching the pH of the intracellular life phenomenon the biological researcher wishes to observe.

As above, the pH probe of the present invention is expected to serve as a useful tool for detailed analysis of various life phenomena.

What is claimed is:

1. A compound represented by the following formula (I):

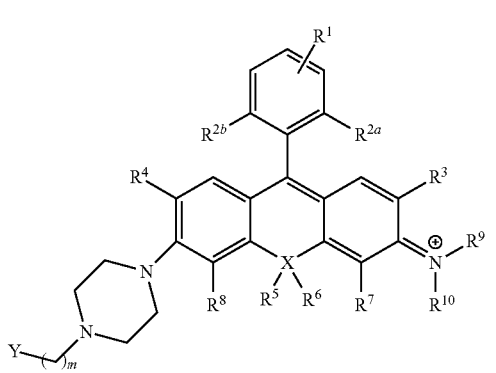

(I)

wherein,
$R^1$ is a hydrogen atom or from one to three of the same or different substituents present on the benzene ring;
$R^{2a}$ and $R^{2b}$ are, each independently, a hydrogen or a substituent, but, $R^{2a}$ and $R^{2b}$ are not both hydrogen;
the substituent of $R^1$, $R^{2a}$, $R^{2b}$ is a substituent defined by either (i) or (ii),
(i) a substituent selected from the group consisting of a $C_{1-6}$ alkyl group, $C_{1-6}$ alkenyl group, $C_{1-6}$ alkynyl group, $C_{1-6}$ alkoxy group, hydroxyl group, carboxyl group, sulfonyl group, alkoxycarbonyl group, halogen atom and amino group;
(ii) a functional group capable of introducing a label site or target accumulation site, and said functional group is selected from the group consisting of a carboxy group, alkyl group having a carboxy group, ester group, alkyl ester group, amino group, amide group, alkylamino group, isothiocyanate group, sulfonyl chloride group, haloalkyl group, haloacetamide group, azide group and alkynyl group;

$R^3$ and $R^4$ are, each independently, a hydrogen atom, $C_{1-6}$ alkyl group, or halogen atom;

$R^5$ and $R^6$ are, when present, each independently, a $C_{1-6}$ alkyl group or aryl group, here, when X is an oxygen atom, $R^5$ and $R^6$ are not present, when X is a phosphorus atom, one of —$R^5$ and —$R^6$ may be =O;

$R^7$ and $R^8$ are, each independently, a hydrogen atom, $C_{1-6}$ alkyl group, or halogen atom;

$R^9$ and $R^{10}$ are, each independently, a hydrogen atom or $C_{1-6}$ alkyl group, $R^9$ or $R^{10}$, together with $R^3$ or $R^7$, may form a five- to seven-membered heterocyclyl or heteroaryl including the nitrogen atoms to which $R^9$ or $R^{10}$ is bonded, may also contain from one to three hetero atoms selected from the group consisting of an oxygen atom, nitrogen atom, and sulfur atom as ring members, and the heterocyclyl or heteroaryl may also be substituted by a $C_{1-6}$ alkyl, $C_{2-6}$ alkenyl, $C_{2-6}$ alkynyl, $C_{6-10}$ aralkyl group, or $C_{6-10}$ alkyl-substituted alkenyl group;

Y is a substituted or unsubstituted aryl group or heteroaryl group;

X is a silicon atom, oxygen atom, carbon atom, phosphorus atom, or germanium atom;

m is an integer of 0-6;

or a salt thereof.

2. The compound according to claim 1, wherein Y is a substituted or unsubstituted phenyl group.

3. The compound according to claim 2, wherein Y is a phenyl group, phenyl group substituted by a fluorine atom, or phenyl group substituted by a sulfonyl group.

4. The compound according to claim 1, wherein m is 0 or 1.

5. The compound according to claim 1, wherein at least one $R^1$ is selected from a carboxy group, alkyl group having a carboxy group, ester group, alkyl ester group, amino group, amide group, alkylamino group, isothiocyanate group, sulfonyl chloride group, haloalkyl group, haloacetamide group, azide group, or alkynyl group.

6. The compound according to claim 5, wherein at least one $R^1$ is a carboxy group, alkyl group having a carboxyl group, amino group, or amide group.

7. The compound according to claim 1, wherein the substituent in $R^{2a}$ and $R^{2b}$ is a $C_{1-6}$ alkyl group, $C_{1-6}$ alkoxy group, or halogen atom.

8. The compound according to claim 7, wherein one of $R^{2a}$ and $R^{2b}$ is hydrogen and the other is a $C_{1-6}$ alkyl group, $C_{1-6}$ alkoxy group, or halogen atom.

9. The compound according to claim 7, wherein both of $R^{2a}$ and $R^{2b}$ are $C_{1-6}$ alkyl groups.

10. The compound according to claim 1, represented by the following formula (II):

(II)

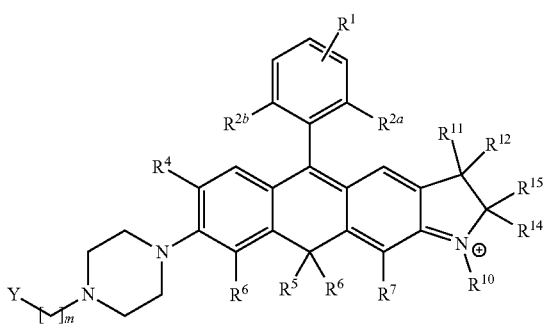

wherein,

R[1]-R[2b], R[4]-R[8], R[10], X, Y, and m are as defined in formula (I), and R[11]-R[14] are, each independently, a hydrogen atom, $C_{1-6}$ alkyl group, or halogen atom.

11. The compound according to claim 10, wherein Y is a substituted or unsubstituted phenyl group.

12. The compound according to claim 11, wherein Y is a phenyl group, phenyl group substituted by a fluorine atom, or phenyl group substituted by a sulfonyl group.

13. The compound according to claim 11, wherein m is 0 or 1.

14. The compound according to claim 10, wherein at least one R[1] is selected from the group consisting of a carboxy group, alkyl group having a carboxy group, ester group, alkyl ester group, amino group, amide group, alkylamino group, isothiocyanate group, sulfonyl chloride group, haloalkyl group, haloacetamide group, azide group, alkynyl group.

15. The compound according to claim 14, wherein at least one R[1] is a carboxy group, alkyl group having a carboxyl group, amino group, or amide group.

16. The compound according to claim 10, wherein the substituent in R[2a] and R[2b] is a $C_{1-6}$ alkyl group, $C_{1-6}$ alkoxy group, or halogen atom.

17. The compound according to claim 16, wherein one of R[2a] and R[2b] is hydrogen and the other is a $C_{1-6}$ alkyl group, $C_{1-6}$ alkoxy group, or halogen atom.

18. The compound according to claim 16, wherein both R[2a] and R[2b] are $C_{1-6}$ alkyl groups.

19. A compound represented by the following formula (Ia):

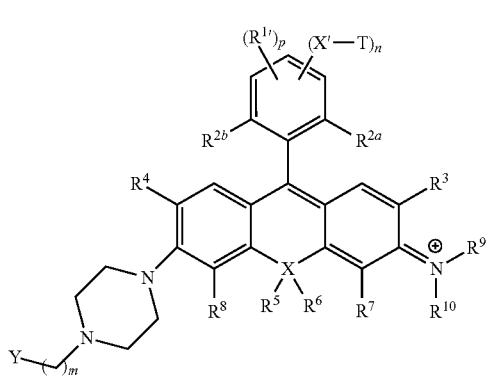

(Ia)

wherein,

R[3] and R[4] are, each independently, a hydrogen atom, $C_{1-6}$ alkyl group, or halogen atom;

R[5] and R[6] are, when present, each independently, a $C_{1-6}$ alkyl group or aryl group, here, when X is an oxygen atom, R[5] and R[6] are not present, when X is a phosphorus atom, one of —R[5] and —R[6] may be =O;

R[7] and R[8] are, each independently, a hydrogen atom, $C_{1-6}$ alkyl group, or halogen atom;

R[9] and R[10] are, each independently, a hydrogen atom or $C_{1-6}$ alkyl group, R[9] or R[10], together with R[3] or R[7], may form a five- to seven-membered heterocyclyl or heteroaryl including the nitrogen atoms to which R[9] or R[10] is bonded, may also contain from one to three hetero atoms selected from the group consisting of an oxygen atom, nitrogen atom, and sulfur atom as ring members, and the heterocyclyl or heteroaryl may also be substituted by $C_{1-6}$ alkyl, $C_{2-6}$ alkenyl, $C_{2-6}$ alkynyl, $C_{6-10}$ aralkyl group, or $C_{6-10}$ alkyl-substituted alkenyl group;

Y is a substituted or unsubstituted aryl group or heteroaryl group;

X is a silicon atom, oxygen atom, carbon atom, phosphorus atom, or germanium atom;

m is an integer of 0-6;

X' is a structure after a functional group capable of introducing a label site or target accumulation site has been bonded with T;

T is a crosslinking group; the crosslinking group may have a functional group capable of introducing a label site or target accumulation site or a functional group capable of bonding with a label site or target accumulation site at one or both ends;

R[1'] are hydrogen or the same or different substituents;

(i) R[2a] and R[2b] are, each independently, hydrogen or a substituent, but, R[2a] and R[2b] are not both hydrogen, or (ii) one of R[2a] and R[2b] is X'-T and the other of R[2a] and R[2b] is a substituent;

n is an integer of 0-2, p is an integer of 1-3, n+p=3;

here, when n is 0, one of R[2a] and R[2b] is X'-T and the other is a substituent;

the substituent of R[1'], R[2a], R[2b] is a substituent selected from the group consisting of a $C_{1-6}$ alkyl group, $C_{1-6}$ alkenyl group, $C_{1-6}$ alkynyl group, $C_{1-6}$ alkoxy group, hydroxyl group, carboxyl group, sulfonyl group, alkoxycarbonyl group, halogen atom and amino group.

20. The compound according to claim 19, represented by the following formula (IIa):

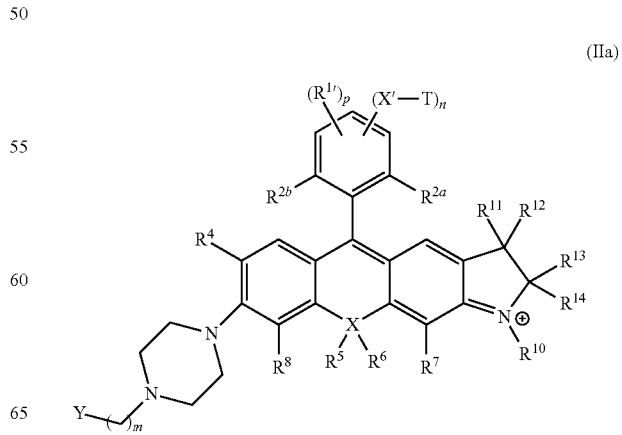

(IIa)

wherein,
$R^4$-$R^8$, $R^{10}$, X, Y, and m are as defined in general formula (Ia);
$R^{11}$-$R^{14}$ are, each independently, a hydrogen atom, $C_{1-6}$ alkyl group, or halogen atom;
X', T, $R^{1'}$, $R^{2a}$-$R^{2b}$, n, and p are as defined in formula (Ia).

21. The compound according to claim 19, wherein —X'-T is selected from the following

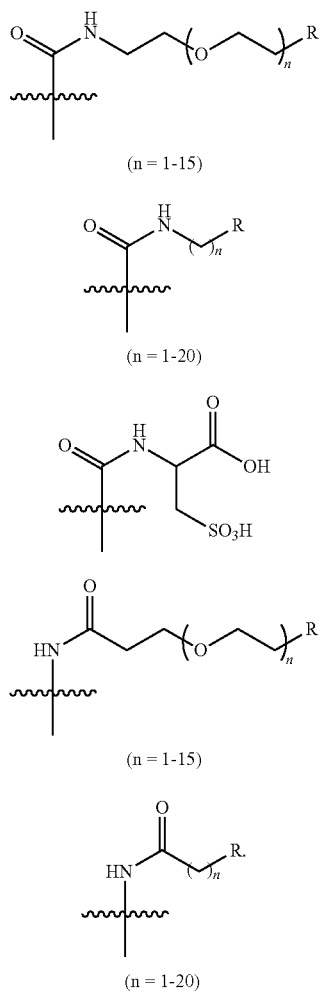

22. A compound represented by the following formula (Ib):

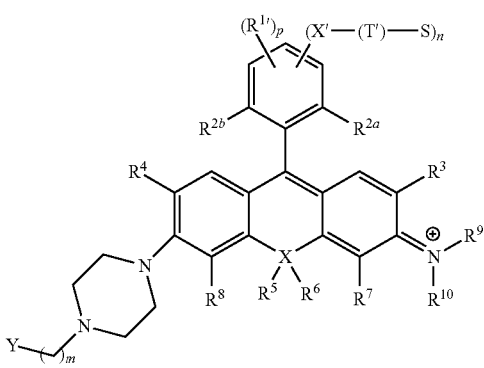

wherein,
$R^3$ and $R^4$ are, each independently, a hydrogen atom, $C_{1-6}$ alkyl group, or halogen atom;
$R^5$ and $R^6$ are, when present, each independently, a $C_{1-6}$ alkyl group or aryl group,
here, when X is an oxygen atom, $R^5$ and $R^6$ are not present,
when X is a phosphorus atom, one of —$R^5$ and —$R^6$ may be =O;
$R^7$ and $R^8$ are, each independently, a hydrogen atom, $C_{1-6}$ alkyl group, or halogen atom;
$R^9$ and $R^{10}$ are, each independently, a hydrogen atom or $C_{1-6}$ alkyl group,
$R^9$ or $R^{10}$, together with $R^3$ or $R^7$, may form a five- to seven-membered heterocyclyl or heteroaryl including the nitrogen atoms to which $R^9$ or $R^{10}$ is bonded, may also contain from one to three hetero atoms selected from the group consisting of an oxygen atom, nitrogen atom, and sulfur atom as ring members, and the heterocyclyl or heteroaryl may also be substituted by $C_{1-6}$ alkyl, $C_{2-6}$ alkenyl, $C_{2-6}$ alkynyl, $C_{6-10}$ aralkyl group, or $C_{6-10}$ alkyl-substituted alkenyl group;
Y is a substituted or unsubstituted aryl group or heteroaryl group;
X is a silicon atom, oxygen atom, carbon atom, phosphorus atom, or germanium atom;
m is an integer of 0-6;
X' is a structure after a functional group capable of introducing a biopolymer label site has been bonded with T;
T', when present, is a structure after a crosslinking group has bonded with S;
S represents a label site or target accumulation site;
$R^{1'}$ are hydrogen or the same or different substituents;
$R^{2a}$ and $R^{2b}$
  (i) are, each independently, hydrogen or a substituent, but, $R^{2a}$ and $R^{2b}$ are not both hydrogen, or
  (ii) one of $R^{2a}$ and $R^{2b}$ is X'-(T')-S and the other of $R^{2a}$ and $R^{2b}$ is a substituent;
n is an integer of 0-2, p is an integer of 1-3, n+p=3;
here, when n is 0, one of $R^{2a}$ and $R^{2b}$ is X'-(T')-S and the other is a substituent;
the substituent of $R^{1'}$, $R^{2a}$, $R^{2b}$ is a substituent selected from the group consisting of a $C_{1-6}$ alkyl group, $C_{1-6}$ alkenyl group, $C_{1-6}$ alkynyl group, $C_{1-6}$ alkoxy group, hydroxyl group, carboxyl group, sulfonyl group, alkoxycarbonyl group, halogen atom and amino group.

23. The compound according to claim 22, represented by the following formula (IIb):

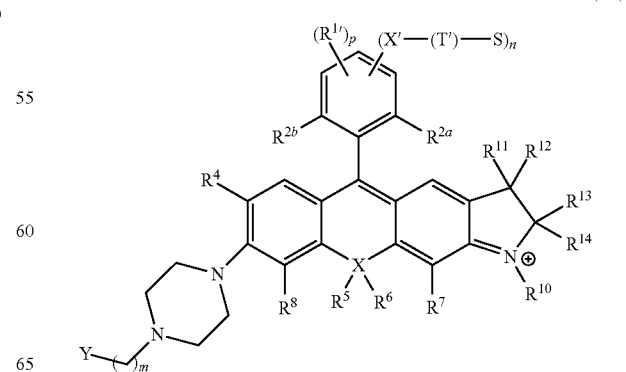

wherein,

R⁴-R⁸, R¹⁰, X, Y, and m are as defined in formula (Ib);

R¹¹-R¹⁴ are, each independently, a hydrogen atom, $C_{1-6}$ alkyl group, or halogen atom;

X', T', R¹', S, $R^{2a}$-$R^{2b}$, n, and p are as defined in formula (Ib).

24. The compound according to claim 22, wherein —S is selected from the following.

(a)
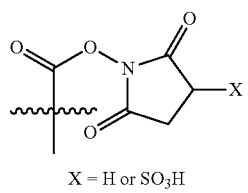
X = H or SO₃H (b)
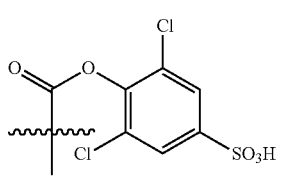

(c)
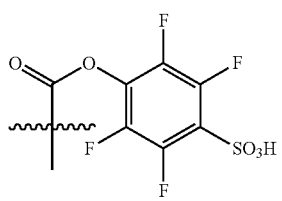

(d)
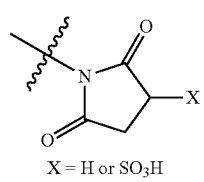
X = H or SO₃H (e)
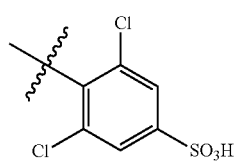

(f)
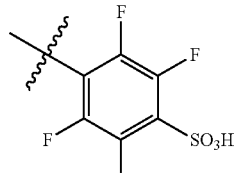

(g)
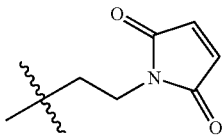

(h)
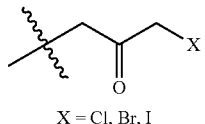
X = Cl, Br, I (i)
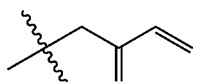

(j)
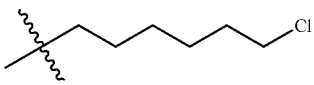

(k)
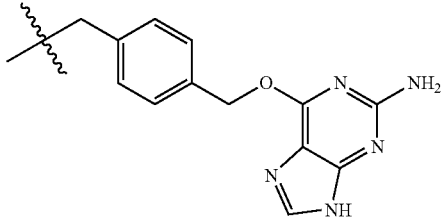

25. A fluorescent probe comprising a compound according to claim 1.

26. A method for measuring an acidic region within a cell, said method comprising;
   (a) a step for introducing the compound according to claim 1 into a cell, and
   (b) a step for measuring the fluorescence emitted within the cell by the compound or salt thereof.

27. The method according to claim 26, the method comprising measuring an acidic region in which an intracellular acidic organelle is present.

* * * * *